United States Patent [19]
Curbelo

[11] Patent Number: 6,025,913
[45] Date of Patent: Feb. 15, 2000

[54] DIGITAL SIGNAL PROCESSING (DSP) TECHNIQUES FOR FT-IR MULTIPLE MODULATION MEASUREMENTS USING A PHOTOELASTIC MODULATOR

[75] Inventor: Raul Curbelo, Lexington, Mass.

[73] Assignee: Bio-Rad Laboratories, Hercules, Calif.

[21] Appl. No.: 09/130,194

[22] Filed: Aug. 5, 1998

Related U.S. Application Data

[60] Provisional application No. 60/055,131, Aug. 8, 1997.

[51] Int. Cl.[7] ........................................ G01B 9/02
[52] U.S. Cl. ................................. 356/346; 250/339.08
[58] Field of Search ..................... 356/346; 250/339.07, 250/339.08, 339.09

[56] References Cited

U.S. PATENT DOCUMENTS

| | | | |
|---|---|---|---|
| 5,036,708 | 8/1991 | Urban et al. | |
| 5,166,749 | 11/1992 | Curbelo et al. | 356/346 |
| 5,262,635 | 11/1993 | Curbelo | 250/214 |
| 5,265,039 | 11/1993 | Curbelo et al. | 364/574 |
| 5,450,196 | 9/1995 | Turner | 356/346 |
| 5,612,784 | 3/1997 | Curbelo | 356/346 |
| 5,835,213 | 11/1998 | Curbelo | 356/346 |

FOREIGN PATENT DOCUMENTS

| | | |
|---|---|---|
| 2728452 | 6/1996 | France . |
| 2 285508 | 9/1994 | United Kingdom . |

OTHER PUBLICATIONS

"Fourier Transform Infrared Spectrometry", Griffiths et al, Chemical Analysis vol. 83, 1996.

Budeveska, Boiana O. et al., "Time–resolved impulse photoacoustic measurements by Step–scan FT–IR spectrometry," *Applied Spectroscopy*, vol. 50, No. 7, pp. 939–947 (1996).

Curbelo, Raul, "Digital signal processing (DSP) applications in FT–IR. Implementation examples for rapid and step scan systems," Proceedings of the Eleventh International Conference on Fourier Transform Spectroscopy, 1997, "AIP Conference Proceedings 430." Editor James A. de Haseth, pp. 74–83, 1998.

Drapcho, David L. et al., "Digital signal processing for step–scan fourier transform infrared photoacoustic spectroscopy," *Applied Spectroscopy*, vol. 51, No. 4, pp. 453–460 (1997).

Hinds International, Inc., "PEM–80™ Photoelastic Modulator Systems Catalog,"1988 (cover and introductory page, pp. 1–21).

Jiang, Eric Y. et al., "Development and applications of photoacoustic phase theory for multilayer materials: The phase difference approach," *J. Appl. Phys.* 78(1), pp. 460–469 (1995).

(List continued on next page.)

*Primary Examiner*—Samuel A. Turner
*Attorney, Agent, or Firm*—Townsend and Townsend and Crew LLP

[57] ABSTRACT

Digital signal proceessing (DSP) techiques for performing multiple modulation measurements with a polarization photoelastic modulator (PEM) in a step-scanning FT-IR spectrometer. The frequency and phase of the PEM drive signal are extracted from the digitized data collected for the actual measurement. This can then be used to perform the desired analysis of the polarization signals (e.g., CD,LD, DIRLD). This is accomplished by successively refining an initial estimate of the PEM frequency (typically starting at the nominal PEM frequency $\omega_0$, or at the value determined from the previous step). This is done by using the current estimate of the PEM frequency to compute a phase error, and then using the computed phase error to refine the estimate of the PEM frequency. The phase errors are computed using different sets of samples in the sampling interval.

15 Claims, 12 Drawing Sheets

OTHER PUBLICATIONS

Kam, P.Y., "Performance of BPSK with open–loop tanlock carrier recovery," *Electronics Letters Online* No. 19950227 (1995).

Manning, Christopher J. et al., "Step–scanning interferometer with digital signal processing," *Applied Spectroscopy*, vol. 47, No. 9, pp. 1345–1349 (1993).

Noda, Isao et al., "A spectrometer for measuring time–resolved infrared linear dichroism induced by a small–amplitude oscillatory strain," *Applied Spectroscopy*, vol. 42, No. 2, pp. 203–216 (1988).

Tervo, Richard et al., "Analysis of digital tanlock loop with adaptive filtering," *IEEE Pacific Rim Conference on Communications, Computers and Signal Proceesing*, vol. 1, pp. 5–8 (1993).

DIGITAL SIGNAL PROCESSING (DSP) TECHNIQUES FOR FT-IR MULTIPLE MODULATION MEASUREMENTS USING A PHOTOELASTIC MODULATOR

CROSS-REFERENCE TO RELATED APPLICATIONS

This application claims priority from U.S. Provisional Application Ser. No. 60/055,131, filed Aug. 8, 1997, of Raul Curbelo, entitled "DSP APPLICATIONS IN FT-IR—IMPLEMENTATION EXAMPLES FOR RAPID SCAN AND STEP SCAN SYSTEMS," the disclosure of which, including all attached documents, is incorporated by reference in its entirety for all purposes.

BACKGROUND OF THE INVENTION

This application relates generally to FT-IR (Fourier transform infrared spectroscopy) and more specifically to multiple modulation measurements with a polarization photoelastic modulator (PEM).

A Fourier transform spectrometer typically includes an interferometer into which are directed a beam of analytic radiation (typically an infrared beam) to be analyzed and a monochromatic (laser) beam that provides a position reference. The interferometer has first and second mirrors.

Each of the input beams is split at a beamsplitter with one portion traveling a path that causes it to reflect from the first mirror and another portion traveling a path that causes it to reflect from the second mirror. The portions of each beam recombine at the beamsplitter, and the recombined beams are directed to appropriate detectors. The difference between the optical paths traveled by the first and second portions of the beams is often referred to as the retardation or retardation value.

One of the mirrors (referred to as the fixed mirror) is fixed or movable over a limited range while the other mirror (referred to as the movable mirror) is movable over a much more extensive range. In rapid scanning, the retardation is changed at a nominally constant rate over a significant range. This is typically accomplished by moving the second mirror at a nominally constant velocity. In step scanning, the retardation is changed intermittently, in relatively small steps of retardation. In some implementations, this is accomplished by stepping the movable mirror position.

The optical interference between the two beam portions causes the intensity of the monochromatic beam and each frequency component of the infrared beam to vary as a function of the component's optical frequency and the retardation. The detector output represents the superposition of these components and, when sampled at regular distance intervals, provides an interferogram whose Fourier transform yields the desired spectrum.

The monochromatic beam provides a reference signal whose zero crossings occur each time the relative position between the fixed and movable mirrors changes by an additional one quarter of the reference wavelength (i.e., for each half wavelength change of retardation). The data acquisition electronics are triggered on some or all of these zero crossings to provide regularly sampled values for the interferogram.

In a step-scan interferometer, the relative position between the fixed and movable mirrors is stepped from one retardation value to the next and then held, at which point an intensity measurement is made. The sequence is then repeated until the desired interferogram has been acquired. The prior art teaches various techniques for accomplishing this under servo control. A number of approaches are disclosed in U.S. Pat. No. 5,166,749 [Curbelo92b], which is incorporated by reference in its entirety for all purposes. Curbelo92b discloses an implementation of step scanning where the movable mirror is driven at a constant velocity and the "fixed" mirror is driven, using an actuator such as a piezoelectric transducer (PZT), in a sawtooth fashion over a small distance corresponding to the desired step size. The superposition of the two movements results in a stepped retardation.

In FT-IR, a PEM is used to modulate the polarization of the spectrometer beam at a PEM drive frequency $f_{PEM}$, to allow the measurement of the difference in the spectral characteristic of the sample to different polarizations ([Noda88], [Hinds88]). A PEM circular dichroism (CD) measurement provides the spectral differential absorption of the sample for left and right circular polarized radiation. The desired signal is obtained by demodulating the spectrometer signal at the PEM drive frequency [Griffiths86]. A PEM linear dichroism (LD) measurement provides the spectral differential absorption of the sample for different linear polarizations, with demodulation at twice the PEM drive frequency. A dynamic infrared linear dichroism (DIRLD) measurement provides the effect on the sample linear dichroism from a dynamic strain modulation at a sample modulation frequency $f_{Sample}$ [Noda88].

In multiple modulation measurements, the data processing system until recently used multiple lock-in amplifiers (LIAs). However, digital signal processing (DSP) techniques are not new in FT-IR [Manning93], and DSP techniques have been used for apodization, Fourier transform, phase correction, and some digital filtering. In a typical DSP solution, all the modulation drive signals are derived from a system master clock, thereby making it possible to demodulate the detector signal's different frequencies using similarly derived signals.

However, PEM measurements present a special problem that suggests that a DSP solution would be unsuitable. In particular, demodulating the PEM carrier signal with a DSP process would require knowing not only the exact frequency of the PEM drive at the time the data was collected, but also its phase relative to the sampling clock. Unfortunately, locking the PEM drive to the system master clock is not practical, as the bandwidth of the PEM is comparable to its resonant frequency drift, and would result in a changing PEM modulation index during a measurement.

SUMMARY OF THE INVENTION

The present invention provides digital signal proceessing (DSP) techiques for performing multiple modulation measurements with a polarization photoelastic modulator (PEM).

In short, the invention measures the frequency and phase of the PEM drive signal from the digitized data collected for the actual measurement. This can then be used to perform the desired analysis of the polarization signals (e.g., CD,LD, DIRLD). While the invention could be carried out with a second digitizer channel in the spectrometer to digitize the signal from the PEM drive, and perform DSP on this signal to acquire the PEM carrier, this is not necessary.

A preferred embodiment recognizes that the PEM carrier (i.e., a signal component at the PEM drive frequency) is typically present in the spectrometer detector signal due to residual polarization in the optical train, or can be added to the spectrometer detector signal in the case where residual polarization has been substantially eliminated. Thus, this embodiment avoids the need to provide a separate hardware channel for digitizing the PEM drive signal.

In a preferred embodiment, the invention successively refines an initial estimate of the PEM frequency (typically starting at the nominal PEM frequency $\omega_0$, or at the value determined from the previous step). This is done by using the current estimate of the PEM frequency to compute a phase error, and then using the computed phase error to refine the estimate of the PEM frequency. In specific embodiments, the phase errors are computed using different sets of samples in the sampling interval.

A method of extracting a modulation frequency according to an aspect of the invention captures a series of discrete digital values output from the detector, the series of discrete values having a time dependence that includes a component resulting from the modulation signal. An initial estimate of the modulation signal is used to process a first subset of the discrete values to determine a first phase error at a first particular point in the sampling interval. This phase error is used to refine the estimate. The refinement may be iterated. The phase error used to refine the frequency estimate represents an estimate of the modulation signal phase. The final refinement of the modulation frequency is preferably based on data taken over the entire sampling interval.

A particular method embodiment includes using a nominal modulation signal at a nominal modulation frequency to process a first subset of the discrete values to determine a first phase error at a first particular point in the sampling interval, using the first phase error and the nominal modulation signal to generate a phase-shifted signal that is nominally in phase with the modulation signal at the first particular point in the sampling interval, using the phase-shifted signal to process a second subset of the discrete values to determine a second phase error at a second particular point in the sampling interval, and using the second phase error to modify the nominal modulation frequency to provide a first refined estimate of the modulation frequency.

The method embodiment may further include using a signal at the first refined estimate of the modulation frequency to process the first subset of the discrete values to determine a first refined phase error, using the first refined phase error to generate a first refined phase-shifted signal, using the first refined phase-shifted signal to process a different subset of discrete values to determine a second refined phase error, and using the second refined phase error to modify the first refined modulation frequency to provide a second refined estimate of the modulation frequency.

According to a further aspect of the invention, a calibration procedure is used to establish the phase delays of the modulation signals that are derived from the system clock. For example, a reference sample having a known phase delay can be implemented by a shutter (partially or fully occluding) attached to the mechanism that stretches the sample at the sample modulation frequency.

Further, the invention addresses and solves a problem where a complex baseline can significantly distort measured values. The baseline contribution to the signal arises from side lobes due to position errors in the interferometer or other departures from ideal behavior. This problem can be particularly acute where there is a small sample modulation. According to the invention, a baseline correction may be determined by demodulating the signal at frequencies on either side of the modulation frequency, and fitting the demodulated values to a function. This function can then be evaluated at the modulation frequency to obtain the baseline correction.

A further understanding of the nature and advantages of the present invention may be realized by reference to the remaining portions of the specification and the drawings.

DESCRIPTION OF SPECIFIC EMBODIMENTS

Terminology

Various terminologies are commonly applied to frequency-related quantities. For example, the character $\omega$ is used in different contexts to represent two different frequency-related quantities. In the continuous frequency domain f represents the frequency in cycles/second (Hz) while ω represents the angular frequency in radians/sec, with the two being related by the well known equation ω=2πf. In the discrete frequency domain, applicable here, ω is given by $2\pi f/f_{Sampling}$, and is thus expressed in radians (radians/sample).

Reference is also made to performing discrete Fourier transforms in connection with the digital signal processing according to the invention. The discrete Fourier transform (DFT) at a particular frequency ω (radians/sample) is usually considered to be performed by multiplying each of a series of samples over a range by $e^{-j\omega n}$, where n is the number of the sample, and then summing the products. For convenience, the specific embodiment described below actually implements what would usually be considered an inverse discrete Fourier transform (IDFT), namely multiplying the value of sample #n by $e^{j\omega n}$, and then performing the summation. For present purposes these operations are equivalent since the difference in sign is accounted for in the other computations.

Incorporation by Reference

The disclosures of all articles and references, including patent documents, mentioned in this application are incorporated herein by reference in their entirety for all purposes.

System Overview

Figure 1:
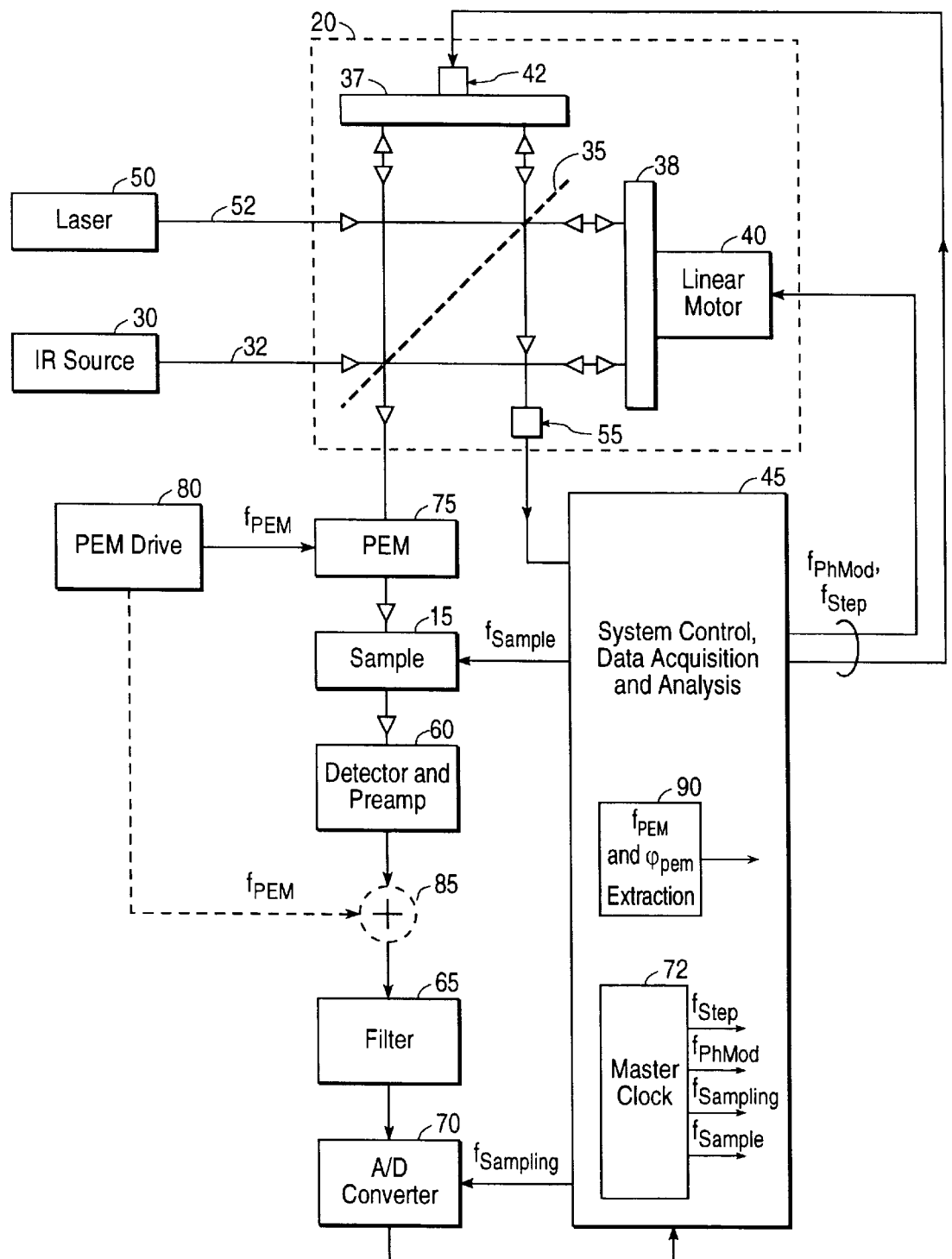
FIG. 1 is a block diagram of an embodiment of a Fourier transform spectrometer system configured for photoelastic modulation (PEM) spectroscopy.

FIG. 1 is a schematic view of a Fourier transform spectrometer system 10 for performing polarization photoelastic modulator (PEM) measurements of a sample 15 in accordance with the invention. Spectrometer system 10 includes a Michelson interferometer 20 and, in a typical embodiment, a broadband infrared source 30, which provides an infrared beam 32. Interferometer 20 comprises a beamsplitter 35, a fixed mirror 37, and a movable mirror 38. The two mirrors are shown at 90° to each other, but in a typical embodiment the mirrors are at approximately 60° to each other (other angles could be used). A linear motor 40, which may include a solenoid drive coil and an air bearing, effects large-scale movement of mirror 38. An actuator 42, preferably a piezoelectric transducer (PZT), is interposed between fixed mirror 37 and the interferometer's fixed structure (not shown), and effects small-scale movement of mirror 37.

Control, data acquisition, and data processing electronics, shown as a system block 45, control the overall operation of the system and provide the data output required by the user. The invention contemplates modifications to the data processing electronics, so that the system, with block 45 incorporating embodiments of the invention, is not prior art. In a specific embodiment, system block 45 includes a general purpose computer.

The underlying purpose of the interferometer in the spectrometer system is to modulate each frequency component of the broadband infrared beam at its own frequency as a function of retardation so that corresponding data at fixed increments of retardation provide interferogram data. Digitized interferogram data is subjected to various data manipulations, including a Fourier transform, to yield the desired spectrum. The particular data manipulations are not part of the invention, and will not be described further. A general description, however, can be found in U.S. Pat. No. 5,262,635 [Curbelo93a], which is incorporated by reference in its entirety for all purposes.

The system further includes a monochromatic reference system to provide signals representing fixed increments of retardation. The monochromatic reference system includes a laser 50, which provides a monochromatic beam 52 impinging on the interferometer.

Infrared beam 32 and monochromatic beam 52 are split at beamsplitter 35 with one portion of each traveling a path that causes it to reflect from fixed mirror 17 and another portion of each traveling a path that causes it to reflect from movable mirror 38. The portions of each beam recombine at beamsplitter 38, and due to optical interference between the two portions, the intensity of each frequency component of the recombined infrared beam and the intensity of the monochromatic recombined beam varies as a function of wavelength and the retardation. The recombined infrared beam is communicated to sample 15 and the recombined monochromatic beam is directed to a monochromatic detector 55. A detector 60 (with associated preamplifier) provides an electrical signal representing the interaction of the recombined infrared beam with the sample. This is typically a measure of the intensity of the light that passes through, reflects from, or scatters from the sample.

The signal from detector 55, when conditioned by the control electronics, provides a reference signal that has a zero crossing every time the retardation changes by half the laser wavelength. The control electronics further operate to provide linear motor 40 with an appropriate voltage waveform to drive mirror 38 in the desired manner.

The drawing is simplified in that the monochromatic reference system and control electronics are also preferably configured to provide alignment corrections. To this end, there are actually three monochromatic detectors and three PZTs configured in a triangular array. Further, the monochromatic beam is broadened so that portions impinge on the interferometer over a broad enough area as to impinge on the three detectors. The three monochromatic detector signals are used by the control electronics to provide signals to the three PZTs to control the angular orientation of fixed mirror 37 and thus compensate for wobble of movable mirror 38 or systematic tilt of the movable mirror or of beamsplitter 35.

For step scanning, which is used in the PEM measurements according to the present invention, linear motor 40 may be driven to step mirror 38 to a series of equally spaced positions with actuator 65 used merely to correct for tilts and wobble as mentioned above. However, as described above in connection with the above mentioned U.S. Pat. No. 5,166, 749, step scanning can be implemented by having linear motor 40 move mirror 38 at a constant velocity and having actuator 42 drive "fixed" mirror 65 in a sawtooth fashion over a distance corresponding to the desired step size.

The analog electrical signal from the detector preamplifier (60) is communicated to a filter 65, the output of which is communicated to an analog-to-digital (A/D) converter 70. In a specific implementation, the filter is an anti-aliasing filter. A/D converter 70 provides a digital signal suitable for further analysis in the general purpose computer in system block 45, possibly assisted by one or more digital signal processors (also referred to as DSPs). In specific implementations, the signal processing is done in the general purpose computer without separate DSPs.

System block 45 includes a master clock 72, which provides a number of timing or clock signals derived from a master oscillator (not shown). These include a step-scanning signal at a frequency $f_{Step}$, a phase modulation (PM) signal at a frequency $f_{PhMod}$, and a sampling signal at a frequency $f_{Sampling}$. For certain types of multiple modulation measurements, a sample modulation signal at a frequency $f_{Sample}$ is also provided. For a DIRLD measurement, the sample modulation is a strain modulation effected by periodically stretching a thin film sample at sample modulation frequency $f_{Sample}$. As is well known the step-scanning signal determines how often the retardation is stepped, while the phase modulation signal provides a dither to the retardation about the nominally fixed value during a step. The sampling signal is used to clock A/D converter 70, and determines the frequency at which the analog signal is sampled to generate digital values for subsequent analysis.

Given that the clock signals discussed above are derived from master clock 72, their frequencies and phases are generally known, and these signals can be used to demodulate the digitized detector signal.

PEM Overview

In order to perform measurements using a photoelastic modulator (PEM), additional elements are interposed in the light path, and possibly in the analog electrical signal path. To this end, a PEM subsystem 75, which includes a PEM and typically one or more polarizing elements, is interposed before the sample in the infrared optical path. The PEM itself is driven by a PEM drive circuit 80 at a frequency designated $F_{PEM}$, which is not derived from or locked to system block master clock 72.

As mentioned above, an aspect of the invention is the manner in which the DSP portion of system block 45 derives PEM drive information. In particular, the invention contemplates measuring the frequency and phase of the PEM drive from the data collected for the actual measurement. In most cases, the PEM carrier is present in the signal due to residual polarization in the optical train. For the case when the residual polarization has been substantially eliminated, a small amount of the PEM drive can be added to the signal, as a pilot carrier, to be used to recover the frequency and phase of the PEM drive. This is shown schematically in FIG. 1 by a dashed connection between PEM drive circuit 80 and a summing node 85 interposed in the analog signal path. The extraction of the PEM frequency and phase is shown schematically as an $f_{PEM}$ extraction block 90.

Figure 2:
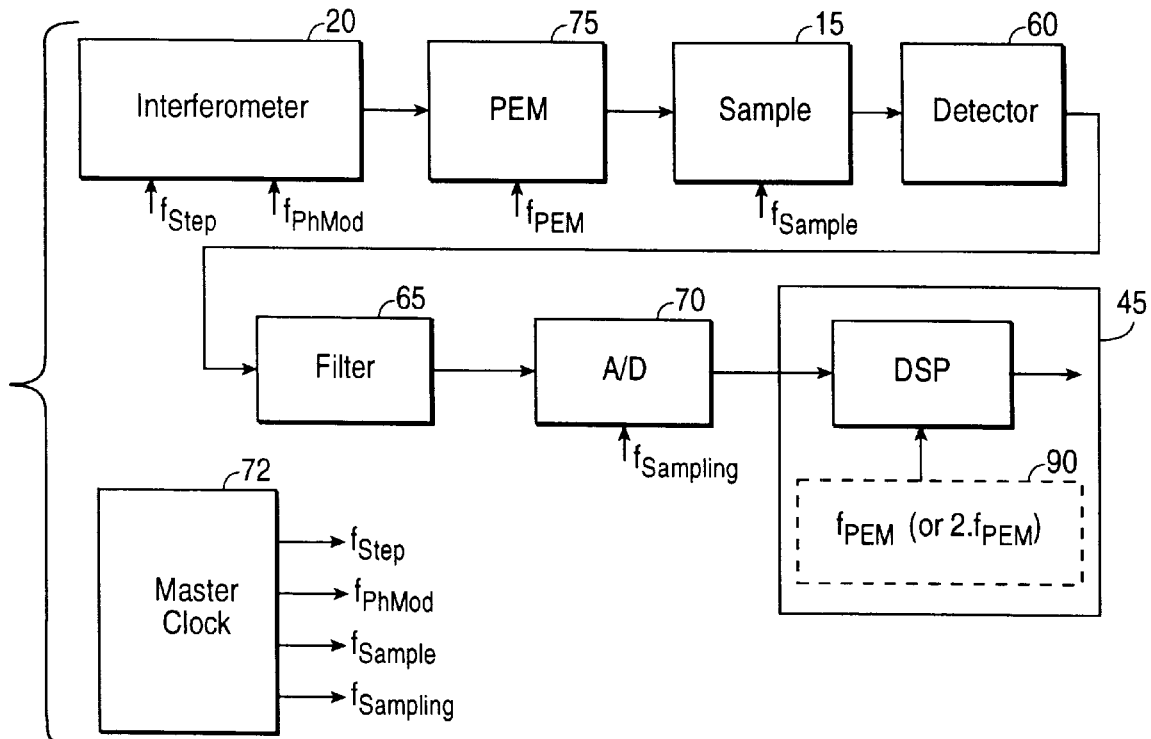
FIG. 2 is a high-level block diagram showing an alternative representation of the system of FIG. 1.

FIG. 2 is a high-level block diagram showing an alternative representation of system 10, showing the manner in which the various modulations are introduced into the system and how the polarization signals are extracted. The demodulation at $f_{PEM}$ or $2.f_{PEM}$ is shown as being performed phantom since the signals for demodulating are derived as part of the DSP itself. FIG. 2 uses corresponding reference numerals for elements corresponding to those in FIG. 1.

Figure 3:
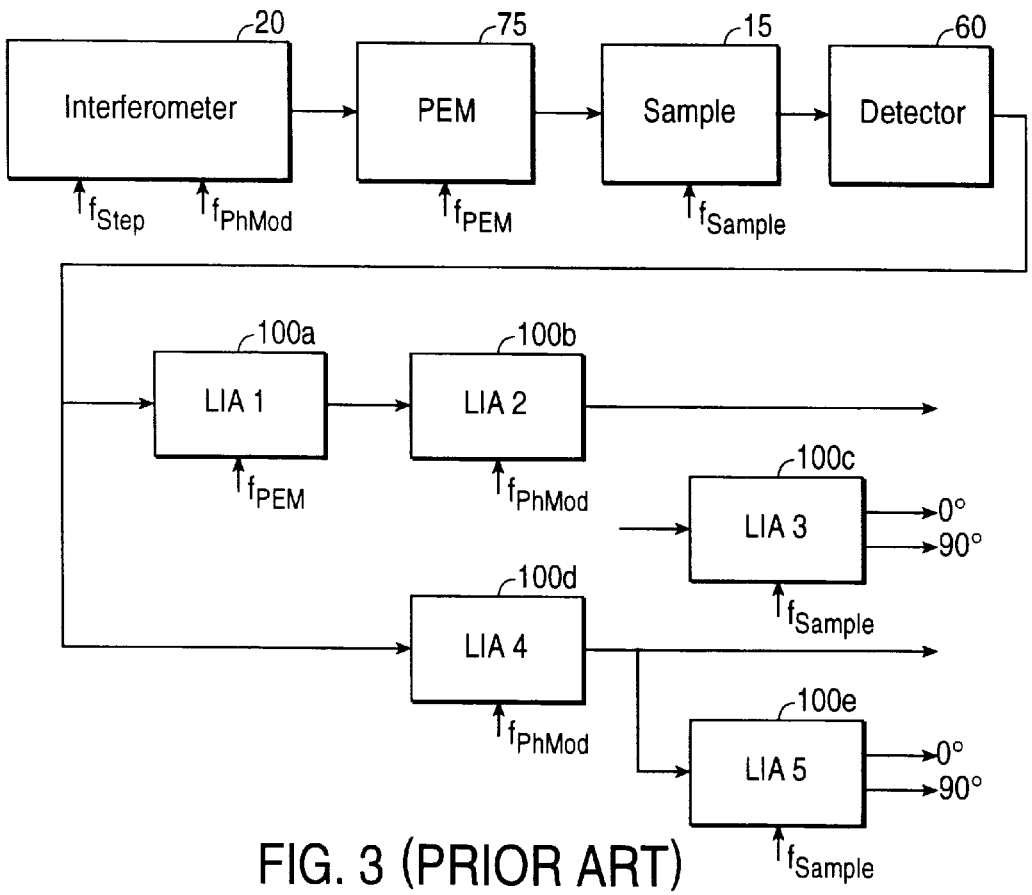
FIG. 3 is a high-level block diagram of a representative prior art system for performing multiple modulation measurements using a plurality of lock-in amplifiers (LIAs)

FIG. 3 is a high-level block diagram of a representative prior art system for performing multiple modulation measurements using a plurality of lock-in amplifiers 100a–e. Elements corresponding to those in FIG. 2 are shown with corresponding reference numerals. In this case, the demodulation at $f_{PEM}$ is straightforward since the demodulation is done prior to digitization, and the PEM drive circuit can be used to provide the demodulation signal.

Figure 4:
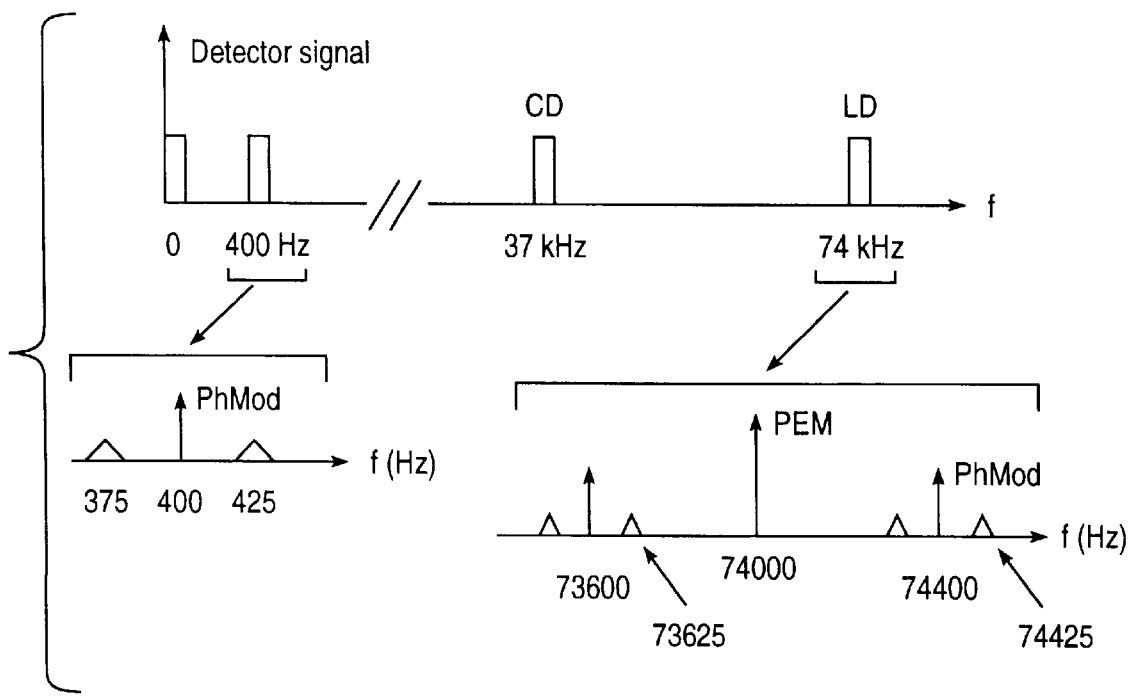
FIG. 4 shows schematically representative spectra for a dynamic infrared linear dichroism (DIRLD) measurement.

FIG. 4 shows schematically representative spectra for the polarization measurements, and more specifically for a dynamic infrared linear dichroism (DIRLD) measurement. In the DIRLD measurement, the information of interest is the effect of the sample modulation (stretch) on the spectral dichroism of the sample. Several measurements are needed to remove the system transfer function from the raw measurement of the dichroic sample modulation. The dynamic absorbance of the sample is measured using a phase modulation frequency that is near the optimum frequency for the detector (400 Hz). Without a phase modulation and with a sample modulation frequency in the tens of Hertz, the detector noise contribution would be more than an order of magnitude larger. The phase modulation shifts the sample modulation signal spectrum to near 400 Hz.

The following modulation frequencies are assumed for the illustration, and are representative of typical implementations:

| | |
|---|---|
| $f_{Step}$ | on order of 1 Hz; |
| $f_{PhMod}$ | 400 Hz; |
| $f_{Sampling}$ | 20 KHz; |
| $f_{Sample}$ | 25 Hz; and |
| $f_{PEM}$ | 37 KHz (nominal). |

For circular dichroism, the polarization signal is present in the sidebands of the carrier at the frequency of the PEM drive, and for linear dichroism, the signal is in the sidebands of the carrier at the second harmonic of the PEM drive. However, as can be seen in FIG. 4, the signals generated, although widely spread in the frequency domain, have quite small actual bandwidth.

Thus, for the case of the circular dichroism measurement the signals of interest are near $f_{PhMod}$ and $f_{PEM}$, while for the case of the linear dichroism measurement (as shown in the figure) the signals of interest are near $f_{PhMod}$ and $2.f_{PEM}$. A nominal value for the PEM drive frequency $f_{PEM}$ is 37 KHz with a tolerance of ±20 Hz. As can be seen from FIG. 4, the signals of interest for DIRLD are actually in the sidebands centered at $f_{PhMod}\pm f_{Sample}$ (375 Hz and 425 Hz) and $2.f_{PEM}\pm f_{PhMod}\pm f_{Sample}$ (73,575 Hz, 73,625 Hz, 74,375 Hz, and 74425 Hz).

Sampling Issues

To sample these signals applying the concept of low-pass sampling, would require a sampling frequency higher than 148 KHz. This rate would generate more than 300 million samples for a low resolution measurement (1000 steps of 1.3 $\mu$m at 1 Hz for 8 cm$^{-1}$ resolution) Considering that the data processing will require on the order of $N^k$ processing operations (where k>1), it is desirable to reduce the number N of samples to be processed for a given measurement.

Figure 5:
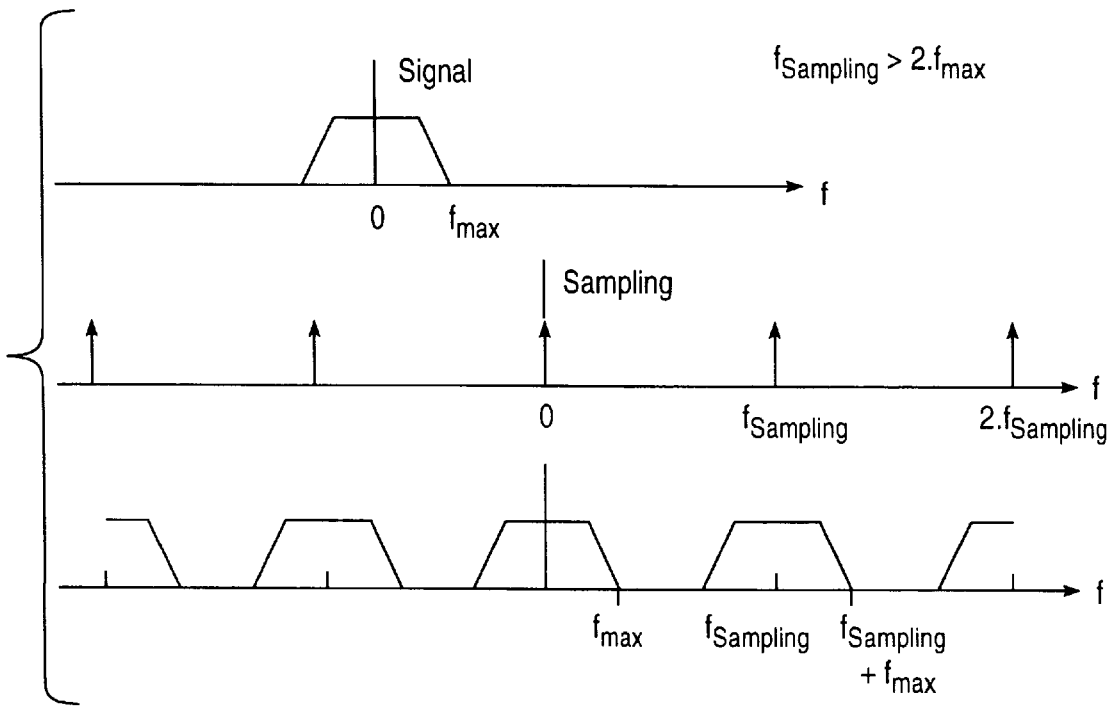
FIG. 5 shows how sampling can be viewed as a modulation process.

FIG. 5 shows how sampling can be viewed as a modulation process in which the spectrum of the sampled signal contains periodic repetitions of the base band spectrum of the sampled signal. In our case the actual signal bandwidth is very small, so the signal can be sampled at substantially lower frequency than $2.f_{max}$.

Figure 6:
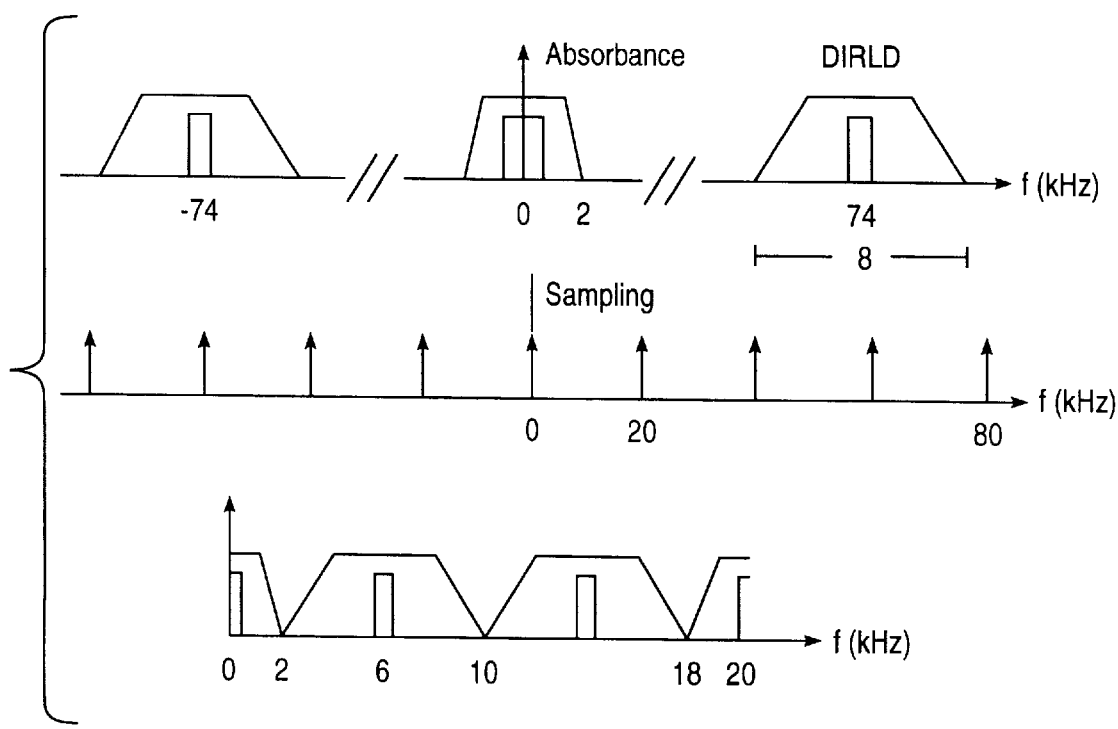
FIG. 6 shows the filter pass bands of an anti-aliasing filter for use with the invention.

FIG. 6 shows the filter pass bands of a fairly simple anti-aliasing filter that will allow sampling at a lower rate and prevent folding of noise over the signal bandwidth. This is feasible because the actual signal bandwidth is much smaller than the separation of the spectral regions of interest. For the linear dichroism measurement using this filter, the signals can be sampled at 20 KHz. As can be seen, the signals near 74 KHz will be translated down to 6 KHz. All other sampling products are at higher frequencies and will be filtered out in the DSP demodulation process at no cost. For the case of circular dichroism, the modulated signals are near 37 KHz and can be sampled at 14 KHz, which will translate the signal down to 5 KHz.

In practice it may be desirable to maximize the effective dynamic range of the A/D converter by oversampling the signal by a factor D (i.e., clocking the A/D converter at $D.f_{Sampling}$), digital low-pass filtering the oversampled digital signal to reduce digitization noise bandwidth (and thus reduce the digitization noise), and decimating the filtered oversampled signal by a factor of D (i.e., selecting one of every D samples of the filtered output). Thus, the samples for subsequent analysis are acquired at an effective sampling rate defined by $f_{Sampling}$ even though the raw digital samples are acquired at $D.f_{Sampling}$.

The digital filtering and decimation can be implemented by averaging each discrete group of D samples, and taking the average values. The averaging implements a simple form of filtering, and since there is one average value for each group of D samples, the decimation occurs automatically. In a particular implementation, the A/D converter operates at 400 KHz, so that D=20 for $f_{Sampling}$=20KHZ.

Oversampling can be made to provide the additional benefit of improving the A/D converter resolution, by adding an electrical or optical dither in the analog signal channel, and averaging the oversampled signal, as described in U.S. Pat. No. 5,265,039 [Curbelo93b]. The dither signal may be random noise or a periodic waveform, and may be generated separately or added inherently by noise in a signal channel having a broadened bandwidth. If no dither is provided, the benefit of oversampling will be limited to the reduction of the digitization noise.

Figure 7:
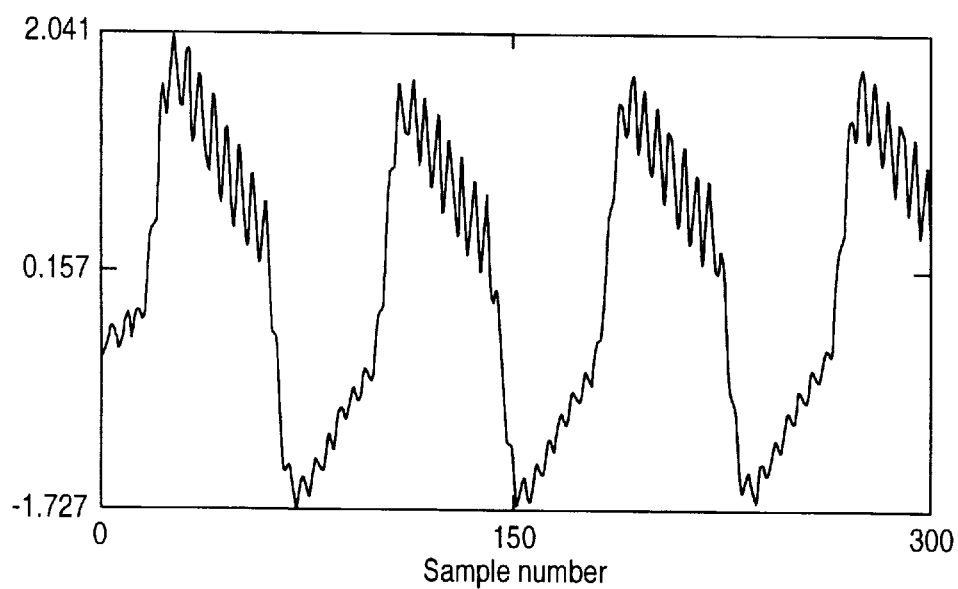
FIG. 7 shows a portion of the sampled signal from a step near the interferogram centerburst.

FIG. 7 shows a portion of the sampled signal from a step near the interferogram centerburst. The PEM carrier signal and the base band phase modulation (PM) signal (distorted square wave) can be recognized.

Extracting the PEM Frequency and Phase

PEM Carrier Extraction Overview

One possible solution, commonly used in the communications field, is to measure the PEM carrier frequency independently. For example, it could be measured at the maximum of the magnitude spectrum of the collected signal in a region centered on the nominal PEM frequency. However, this method is unlikely to be suitable since it will tend to be severely limited by the signal-to-noise ratio of the signal, and in general will have substantial errors.

The explanation of the signal processing that provides the desired demodulations of the digitized signal makes use of a number of discrete domain frequencies (all ω variables in radians/sample), which are related to the frequencies discussed above as follows:

| | |
|---|---|
| $\omega_{phmod}$ | $2\pi\ f_{PhMod}/f_{Sampling}$; |
| $\omega_{sample}$ | $2\pi\ f_{Sample}/f_{Sampling}$; |
| $\omega_0$ | $2\pi\ f_{PEMo}/f_{Sampling}$ (nominal); and |
| $\omega_{pem}$ | $2\pi\ f_{PEM}/f_{Sampling}$. |

FIGS. 8–12 show elements of a preferred technique for determining the PEM carrier frequency and phase based on the actual sampled signal for a given interferometer step. This determination is made after the data samples have been acquired for the interferometer step. In a particular implementation, all processing, including the PEM carrier determination, is performed-at the end of each scan. As will be described below, a preferred technique for determining the phase used in the DSP demodulation process requires information from more than a single step (preferably an entire scan).

In short, this technique successively refines an initial estimate of the PEM frequency (typically starting at the nominal PEM frequency $\omega_0$). This is done by using the current estimate of the PEM frequency to compute a phase error, and then using the computed phase error to refine the estimate of the PEM frequency. The phase errors are computed using different sets of samples in the sampling interval. This embodiment assumes an approximately constant PEM frequency over the sampling interval for the interferometer step. That is, it is assumed that the phase is an approximately linear function of time (sample number). However, there is no assumption that the PEM frequency is constant from step to step.

Sequence of Processing Steps

Figure 8:
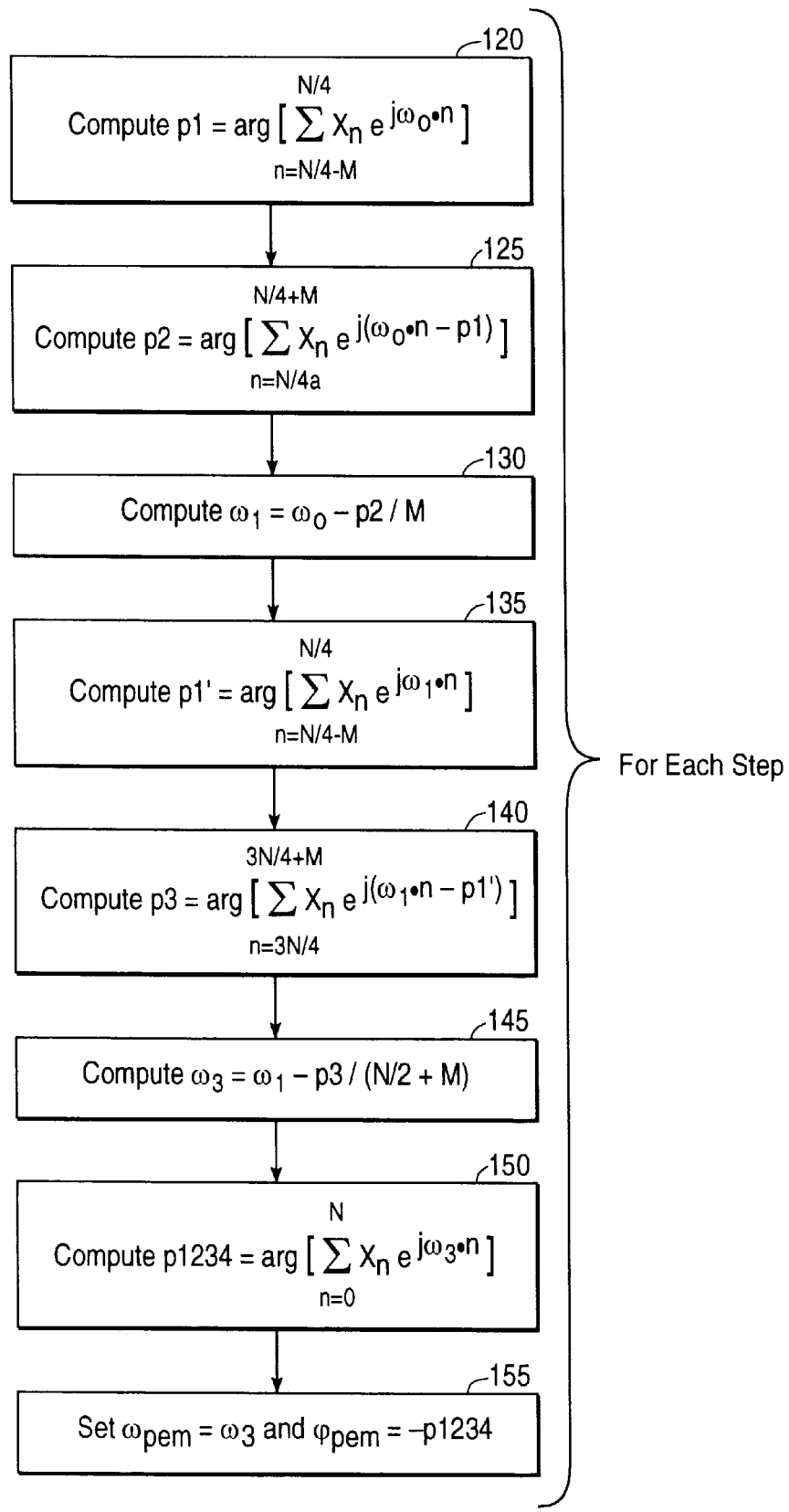
FIG. 8 is a flowchart showing the extraction of the PEM carrier phase and frequency.

FIG. 8 is a flowchart showing a specific implementation of PEM extraction block 90 (shown in FIG. 1) for extracting the PEM carrier phase and frequency from portions of the digitized detector signal for a single interferometer step.

Figure 9:
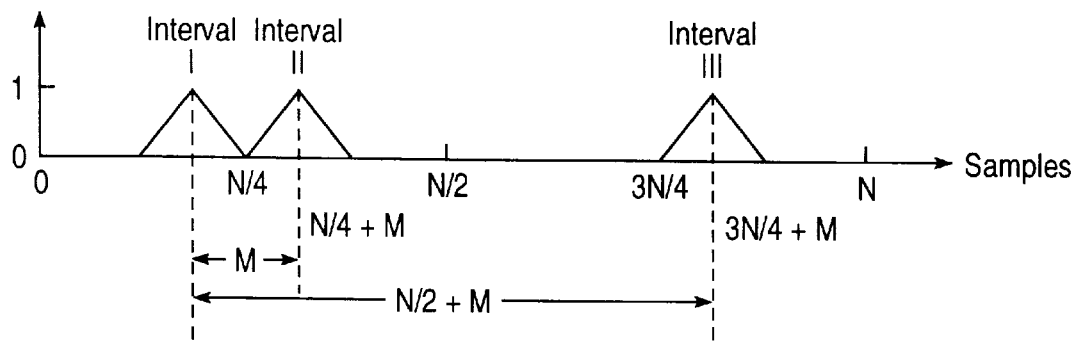
FIG. 9 shows a first stage of the processing for extracting the PEM frequency and phase.

FIG. 9 shows the first stage of the processing where three sets of M samples out of the N samples from the first step of the interferometer scan are selected. The three intervals are designated intervals I, II, and III, and are defined as follows:

| | |
|---|---|
| I | samples N/4 − M to N/4 |
| II | samples N/4 to N/4 + M |
| III | samples 3N/4 to 3N/4 + M |

In specific implementations, each set is apodized, for example with a triangular window function. These samples are referred to as $X_n$ where "n" is the sample number in the interferometer step. As will be desribed in detail below, at various stages, a phase error is computed by performing a DFT on a set of samples using a current estimate of the PEM frequency.

Figure 10:
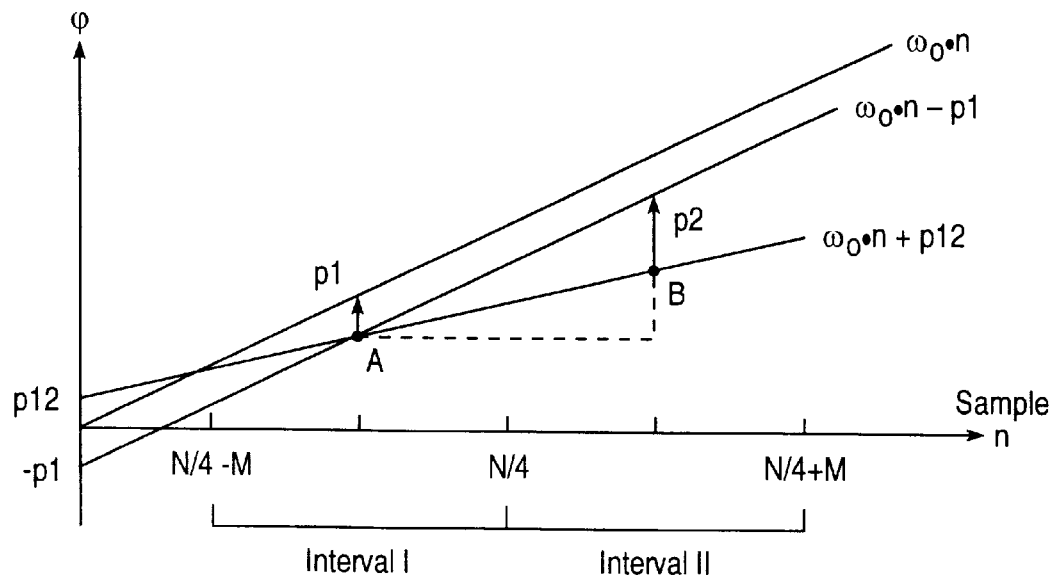
FIG. 10 is a plot of phase angle $\phi$ as a function of sample number for a number of signals that are generated (computed) in the course of determining the PEM frequency and phase.

FIG. 10 is a plot of phase angle φ as a function of sample number for a number of signals that are generated (computed) in the course of determining the PEM frequency and phase. Each line represents a different signal, with the slope being proportional to the signal's frequency and the intercept with the vertical axis being the signal's phase at the beginning of the sampling interval. The line passing through the origin and labeled "$\omega_0.n$" at its end denotes a signal of φ=0 for n=0 (zero phase for sample 0) at the nominal PEM frequency $\omega_0$. This line is characterized by the equation φ=$\omega_0$.n. This signal is the initial estimate of the PEM carrier signal, and is successively refined as follows. For purposes of illustration, it is assumed that the actual PEM carrier frequency is less than $\omega_0$.

First, at a processing block 120, the phase error between this signal and the samples in interval I is computed. The calculated quantity represents the phase difference between this signal at nominal PEM frequency $\omega_0$ and the actual PEM carrier signal at the center of interval I. This phase error is designated p1.

Particular DSP for Computing Phase Errors

Figure 11:
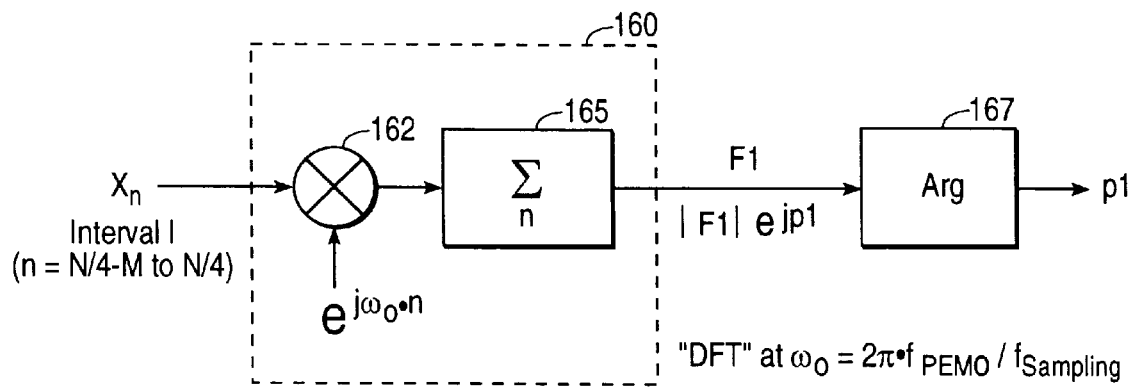
FIG. 11 is a schematic of a processing block's DSP computation of a phase error.

FIG. 11 is a schematic of processing block 120's DSP computation of phase error p1 using the set of samples in interval I, and the signal with the nominal PEM frequency $\omega_0$ (in radians/sample) and with a phase of 0 for n=0. Phase error p1 is determined by computing the discrete Fourier transform (DFT) F1 of the samples $X_n$ in interval I at $\omega_0$, and then computing the argument (phase angle) of F1. The argument, so computed, is p1.

The figure shows schematically a DFT block 160 comprising a complex multiplier 162 and a summing block 165, the output of which is communicated to an argument computation block 167. DFT block 160 effects the multiplication of each sample (preferably apodized) by the complex exponential and the summation over samples. The figure has DFT in quotation marks since it could be thought to be an IDFT, as mentioned above. As is well known, a complex number can be expressed by its magnitude (absolute value) times the complex exponential of its argument (phase angle). Thus, for the specific instance, F1=|F1|.$e^{jp1}$. In the general case, the line for this nominal PEM signal has a different slope and intercept than the line for the actual PEM carrier since, in the general case, the nominal PEM frequency and zero phase are different from the actual PEM frequency and phase. It will-be appreciated that the complex multiplier shown in this DSP block and various other DSP blocks has the effect of multiplying an input signal by a sine and cosine, so that the real and imaginary parts are effectively the in-phase and quadrature components.

Initial Refinement

Although the actual PEM frequency and phase are as yet unknown, if the DFT for the same set of samples were to be recomputed with $e^{j(\omega_0 n - p1)}$ the resulting argument would be zero. That is, a signal characterized by a frequency $\omega_0$ with phase $-p1$ (at $n=0$) would be in phase with the PEM carrier at the center of interval I. The line for this signal has the equation $\phi = \omega_0 \cdot n - p1$, and is represented in FIG. 10 by a line labeled "$\omega_0 \cdot n - p1$." While the signal represented by this line still has the nominal PEM frequency, it carries some PEM carrier information since it now passes through a point A at the center of interval I where it is nominally in phase with the PEM carrier.

Next, at a processing block 125, a point that is nominally in phase with the PEM signal at the center of interval II is determined by computing the phase error p2 between the signal at the nominal PEM frequency and phase $-p1$ and the samples in interval II.

Next, at a processing block 130, the value of p2 is used to compute a better estimate $\omega_1$ of the PEM frequency as shown in equation 1. That is, p2 is used to refine the initial estimate $\omega_0$. (All equations unless indicated use $\omega$ in radians/sample, which is the abscissa of the DFT)

$$\omega_1 = \omega_0 - p2/M \qquad (1)$$

The computation of p2 is as discussed above, except using $e^{j(\omega_0 \cdot n - p1)}$. That is, the phase error is calculated by computing the DFT F2 at $(\omega_0 \cdot n - p1)$ and then computing the argument of F2. The argument, so computed, is p2. A point B at the center of interval II and P2 below the line labeled "$\omega_0 \cdot n - p1$" in FIG. 10 represents a point that is nominally in phase with the PEM signal. A line passing through points A and B represents a signal that more closely approximates the PEM carrier signal. $\omega_1$ represents the slope of this line, and equation 1 is derived by calculating the slope of the hypotenuse of the right triangle shown with its base and altitude in dashed lines. The base is M, and the altitude is $\omega_0 \cdot M - p2$. The line intercepts the vertical axis at a phase p12, and the line is labeled "$\omega_1 \cdot n + p12$."

Next, at a processing block 135, using the value of $\omega_1$, the phase error p1' of a signal with frequency $\omega_1$ and $\phi=0$ for $n=0$ in interval I is recomputed. In the specific embodiment, this is accomplished in the same manner as the initial computation of p1, but using $\omega_1$ instead of $\omega_0$ in the computaion. It is noted, however, that there is another way of doing this. As can be seen from FIG. 10, the intercept p12 represents another estimate of the PEM phase, and can be calculated by simple geometry. While this is likely to require less computation than calculating the estimate of the PEM phase using the DFT, the latter has the advantage that it invokes a software routine that is already needed for other purposes. It should be noted that the intercept is the negative of the calculated phase error. Thus p12=-p1'.

Further Refinement

Next, at a processing block 140, using the value of p1', the phase error p3 in interval III is computed using $e^{j(\omega_1 \cdot n - p1')}$. That is, the computation is like that shown in FIG. 11, except that $\omega_1$ is used instead of $\omega_0$ and the samples in interval III (3N/4 to 3n/4+M) are used. Next, at a processing block 145, the value of phase error p3 is used to refine the estimate of the PEM frequency as shown in Equation 2.

$$\omega_3 = \omega_1 - p3/(N/2+M) \qquad (2)$$

Another iteration may be required depending on the value of M used. The order of magnitude of the remnant error can be estimated using $|\omega_3 - \omega_1|$. M must be small enough so $p2 < \pi$, and large enough so $p3 < \pi$, for equations 1 and 2 to be valid. The first condition is met if:

$|\omega_{pem} - \omega_0| \cdot M < \pi$, or equivalently, $$M < f_{sampling}/(2 \cdot |f_{PEM0}|) \qquad (3)$$

The second condition is met if:

$|\omega_{pem} - \omega_1| \cdot N/2 < \pi$, or equivalently, $$N < f_{sampling}/(2 \cdot |f_{PEM} - f_1|) \qquad (4)$$

where $f_1$ corresponds to $\omega_1$.

If the second condition is not met, a second iteration in equation 1 is required with a larger interval length M', to obtain a better estimate of $\omega_{pem}$. At the same time, to optimize the convergence of the measurement of $\omega_{pem}$, M should be selected so the spectrum of the apodized signal has a minimal contribution at the PM sideband frequency. The spectrum of a signal apodized with a triangular function of a time interval $M/f_{sampling}$ has zeros at $2 \cdot k_1 \cdot f_{sampling}/M$, where $k_1$ is an integer. For the PM frequency $f_{phMod}$ M can be selected so that:

$$M = 2 \cdot k_1 \cdot f_{sampling}/f_{PhMod}$$

For example, for $f_{Sampling}$=20 KHz, $f_{PEM}$=6 KHz (as translated down from 74 KHz by the sampling), $|f_{PEM} - f_{PEM0}| < 20$ Hz, and $f_{PhMod}$=400 Hz, M can be a multiple of 100, no larger than 500.

Next at a processing block 150, the value of $\omega_3$ is used to compute the phase error p1234 for the entire array (all N samples in the sampling interval). This is preferably done using an apodization function $A_n$ selected to provide filtering in the frequency domain, when demodulating the sideband information from the PEM and PM modulations.

The apodization function $A_n$ should provide substantial attenuation to the sidelobes of the different components of the signal, and in particular at or near $\omega_{phmod}$ and $\omega_{sample}$. A simple first choice is a triangular apodization. The Fourier transform is of the form:

$$|A(\omega)| = C \cdot \sin^2(k_N \cdot \omega)/(k_N \cdot \omega)^2$$

Figure 12:
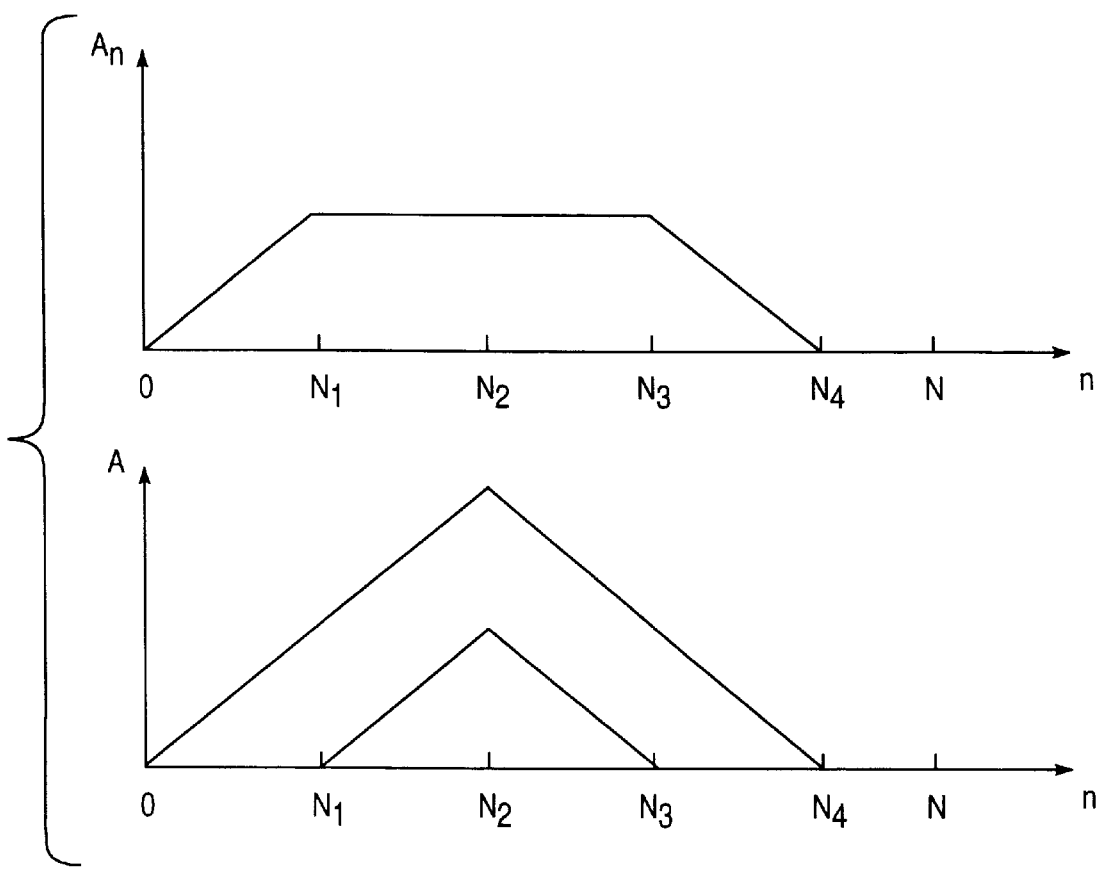
FIG. 12 shows a trapezoidal apodization function as the difference between two triangular functions.

FIG. 12 shows another useful function $A_n$, namely a trapezoid, which is shown in the upper portion of the figure. The trapezoid can be considered as the difference between the two triangular functions shown in the lower portion of the figure. $N_1$, $N_2$, $N_3$, and $N_4$ are selected so the Fourier transform of $A_n$, which has the form:

$$A(\omega) = C \cdot \sin^2(k_N \cdot \omega)/(k_N \cdot \omega)^2 - \sin^2(k_L \cdot \omega)/(k_L \cdot \omega)^2$$

has zeros in both terms at $\omega_{sample}$ and at or near $\omega_{phmod}$.

Thus, the determination of $\omega_3$ has provided a close estimate of the PEM frequency, and the determination of phase error p1234 has provided a close estimate of the PEM phase. This is shown schematically in FIG. 8 as a processing block 155, where $\omega_{pem}$ is set to $\omega_3$ and $\phi_{pem}$ is set to $-p1234$. This now allows correct demodulation of the signal at the PEM frequency for that step of the interferogram.

For successive steps, the values of $\omega_{pem}$ and 100 $_{pem}$ are preferably measured using the process above, but preferably using the previous step's $\omega_{pem}$ value for the initial estimate.

Since the PEM drive frequency would likely have drifted only a small fraction of a Hertz in the time of one step, it is likely that only the last iteration will be required to obtain a sufficiently accurate estimate of $\omega_{pem}$.

Overall Demodulation Processing

Block Diagram View

Figure 13:
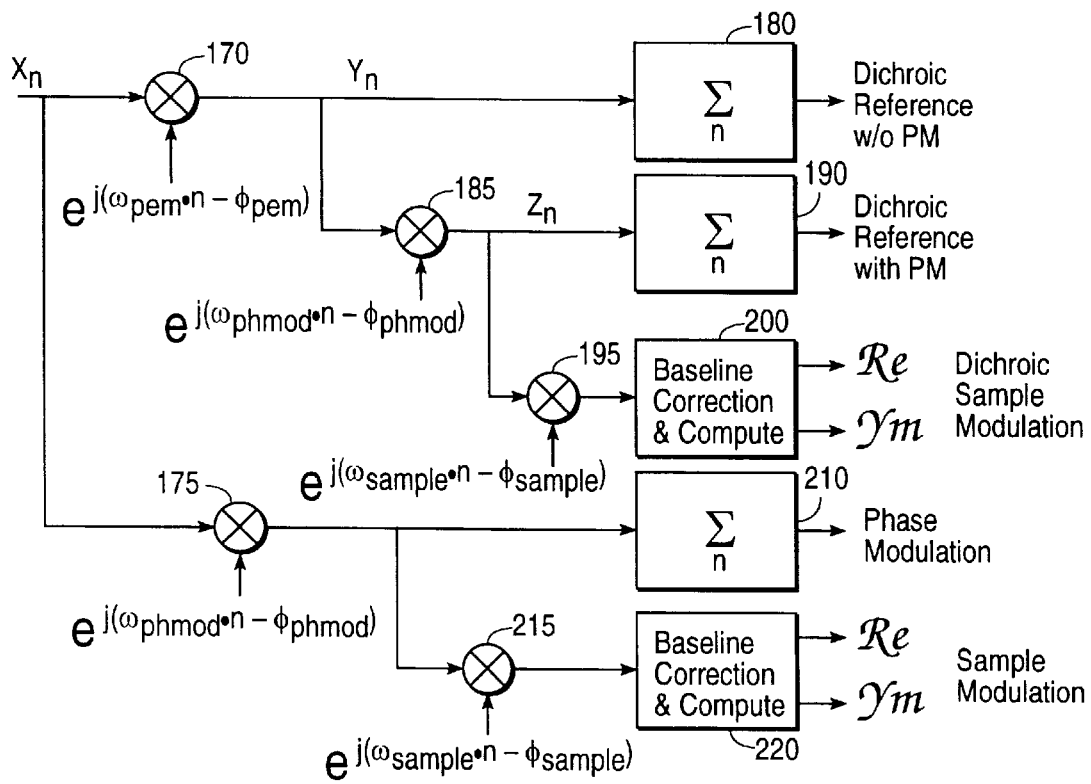
FIG. 13 is a block diagram showing the DSP for a typical triple modulation measurement for a single step.

FIG. 13 is a block diagram showing the DSP for a typical triple modulation measurement for a single step. The figure shows demodulation at the frequencies $\omega_{pem}$, $\omega_{phmod}$, and $\omega_{sample}$. Proper demodulation also requires the proper phase for each demodulating signal. The phases are denoted $\phi_{pem}$, $\phi_{phmod}$, and $\phi_{sample}$. The PEM carrier phase $\phi_{pem}$ is determined for each step as described above. The need for the other phase quantities $\phi_{phmod}$ and $\phi_{sample}$ arises from the fact that while the modulation and demodulation signals are derived from the same master clock, the carrier at each of the frequencies $\omega_{phmod}$ and $\omega_{sample}$ will not in general be in phase due to delays in the electronics and possible sample-induced delays. Procedures for measuring these phases using a reference sample will be described in more detail below.

The samples $X_n$, preferably apodized, are communicated to a PEM complex multiplier 170 and to a phase modulation complex multiplier 175. The output values from complex multiplier 170, designated $Y_n$, are communicated to a first summing block 180 and to a second phase modulation complex multiplier 185. The output values from complex multiplier 185, designated $Z_n$, are communicated to a second summing block and to a sample modulation complex multiplier 195. The output values from complex multiplier 195 are communicated to a processing block 200.

The output values from complex multiplier 175 are communicated to a third summing block 180 and to a second sample modulation complex multiplier 215. The output values from complex multiplier 215 are communicated to a second processing block 220.

Summing blocks 180 and 190 provide dichroic reference information, with and without phase modulation. The output of summing block 180 is the total optical anisotropy of the system [Noda 88]. This measurement is only used for diagnostic purposes in this particular instance since none of the processing blocks is providing information resulting from demodulation at the sample modulation frequency without demodulation at the phase modulation frequency. The output from summing block 190 for a sample of known anisotropy is used as a reference for the sample dynamic dichroic spectral response provided by processing block 200.

The measurement of the sample dynamic absorbance obtained in processing block 220 must be referenced to the spectral transmittance of the system at the frequency of the phase modulation, which is obtained in summing block 210, by demodulating the detector signal at the phase modulation frequency. That is, the output from summing block 210 is used as a reference for the sample modulation measurement values provided by processing block 220.

As mentioned above that the output from each of the summing blocks and processing blocks represents information for a single step. Ultimately, this information is provided as respective single points to respective interferograms. For example, the dichroic reference with phase modulation from summing block 190 is a real number, that when combined with the corresponding outputs from other steps leads to a real interferogram. When processed, this real interferogram provides a real reference spectrum. Similarly, the output from processing block 200 includes real and imaginary parts representing the dichroic sample modulation, and the real and imaginary parts, when combined with the corresponding outputs from other steps, lead to real and imaginary interferograms. When processed, these interferograms result in real and imaginary spectra (in-phase and quadrature spectra). These spectra are divided by the reference spectrum to provide the desired output representing the desired dichroic sample modulation spectra. Similar comments apply to the outputs from summing block 210 and processing block 220. In this case, the ultimate spectra are the real and imaginary (in-phase and quadrature) spectra representing the effect of sample modulation with phase modulation.

Spectral View

Figure 14:
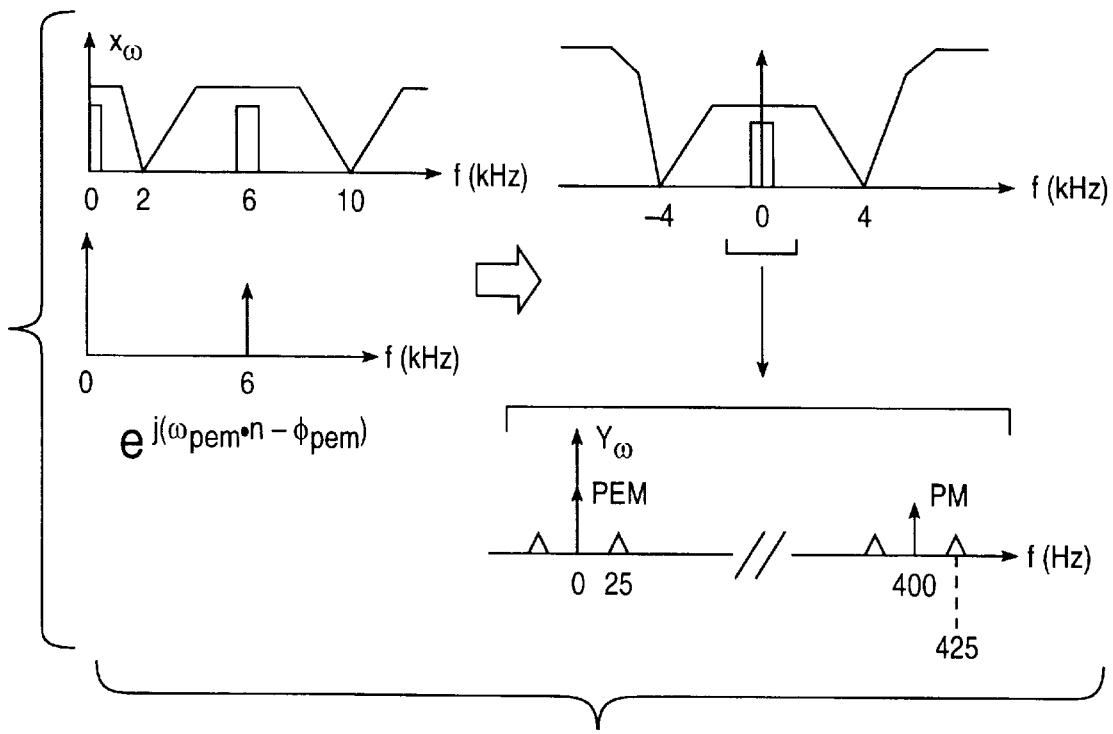
FIG. 14 shows frequency transformations effected by portions of the DSP shown in FIG. 13.

FIG. 14 shows, in the spectral domain, the frequency transformations effected by complex multiplier 170 (operating at the PEM carrier frequency and phase) as shown in FIG. 13. FIG. 14 represents the first of a series of successive demodulations performed to extract the PEM information. As mentioned in connection with FIGS. 4 and 6, the PEM information of interest lies in various sidebands in the neighborhood of $2 \cdot f_{PEM}$ (74 KHz, which is translated down to 6 KHz by the sampling). The extraction of the information of interest, as seen in FIG. 13, includes various combinations of demodulations of the input signal to bring the sidebands down to baseband (a frequency range centered around zero). The summation or other processing of the samples over the sampling interval then provides a numerical value that represents the quantity to be measured. As mentioned, the results of the DSP at each step provide respective values for respective single points in a set of interferograms.

The top left segment of FIG. 14 replicates a portion of the bottom segment of FIG. 6 and shows the PEM information of interest in a band at 6 kHz. The trapezoidal shapes represent the anti-alias filter that prevents noise from folding into the spectral range of interest.

The lower left segment of FIG. 14 shows the spectrum of the derived PEM carrier. As is well known, demodulation of signals of interest near a carrier frequency generates signals at the sum and difference of the frequencies, thereby translating the signals of interest to baseband and to a range centered at twice the carrier frequency. Only the region around zero frequency is of interest, as shown in the top right segment of FIG. 14. The lower right segment of FIG. 14 represents an enlarged view of this region the region around zero, which includes sidebands around the translated carrier (at zero) and sidebands around the $f_{PhMod}$ (400 Hz). The sidebands at −25 Hz and 25 Hz represent the combination of the PEM and sample modulations without phase modulation, while the sidebands about 400 Hz represent the combination of the PEM modulation, the phase modulation, and the sample modulation. A further, demodulation at f od as effected by complex multiplier 185 in FIG. 13 (but not shown in FIG. 14), would translate the sidebands around 400 Hz down to 25 Hz on each side of zero. A further demodulation at $f_{sample}$ (25 Hz), as effected by complex multiplier 195 in FIG. 13 (but not shown in FIG. 14), would bring the sidebands down to a narrow region centered about zero frequency.

Determining Phases for Demodulation at $f_{PhMod}$ and $f_{Sample}$

Figure 15:
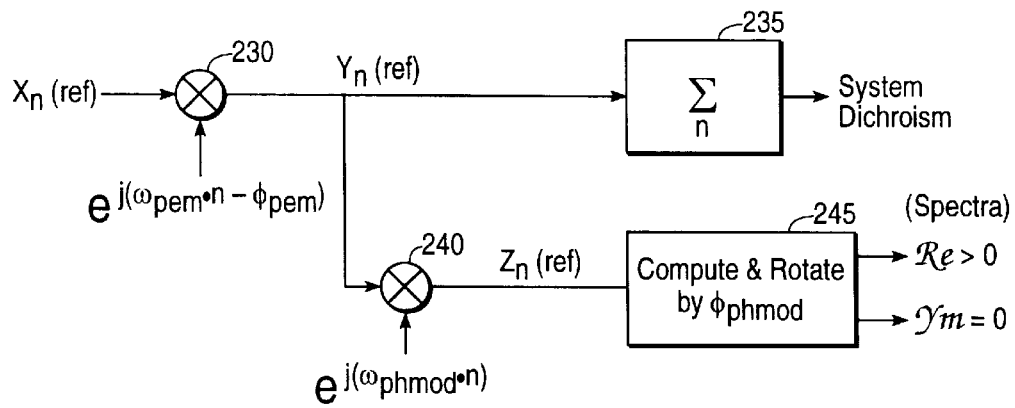
FIG. 15 is a block diagram showing a portion of the DSP for extracting the phase needed for demodulation at the phase modulation frequency.

FIG. 15 is a block diagram showing a portion of the DSP for extracting the phase $\phi_{phmod}$ needed for demodulation at the phase modulation frequency $\omega_{phmod}$. As mentioned above, while the phase modulation and sample modulation frequencies are known, since they are derived from the same master clock that generates the modulation signals, the phases of the appropriate demodulation signals are not known in advance due to delays and the like in the analog and digitization signal paths.

These phases are preferably determined by performing a calibration with a reference sample whose phase characteristics are known. It is then possible to determine the system-induced phase delays by processing the digitized signal generated using the reference sample. The term "reference sample" is used in a broad sense, because for the $\phi_{phmod}$ determination, the reference sample is no sample at all, i.e., open beam. This "sample" clearly introduces no phase shift. A suitable reference "sample" for the $\phi_{sample}$ determination is a solid blade driven by one jaw of the mechanical film stretcher that is used to stretch the sample for the sample modulation. If other types of sample modulation were to be used, the reference would typically be different. For example, if the sample modulation were effected by applying an electric field, a possible reference sample might be a liquid crystal device (whose transmission varies with the electric field). The phase delay for the reference sample would have to be measured separately (typically outside the interferometer).

While the previous descriptions of the DSP were primarily for a single step, the calibration requires data from several or all steps in a scan. The samples $X_n(\text{ref})$ taken using the reference sample and preferably apodized, are communicated to a PEM complex multiplier 230, which uses the previously determined values for $\omega_{pem}$ and $\phi_{pem}$ (separately determined for each step). The output values from complex multiplier 230, designated $Y_n(\text{ref})$, are communicated to a summing block 235 and to a phase modulation complex multiplier 240. Complex multiplier 240 uses only the known value for $\omega_{phmod}$ since $\phi_{phmod}$ is not yet known. The output values from complex multiplier 240, designated $Z_n(\text{ref})$, are communicated to a processing block 245. Processing block 245 uses the $Z_n(\text{ref})$ data to compute the desired $\phi_{phmod}$ value.

Figure 16:
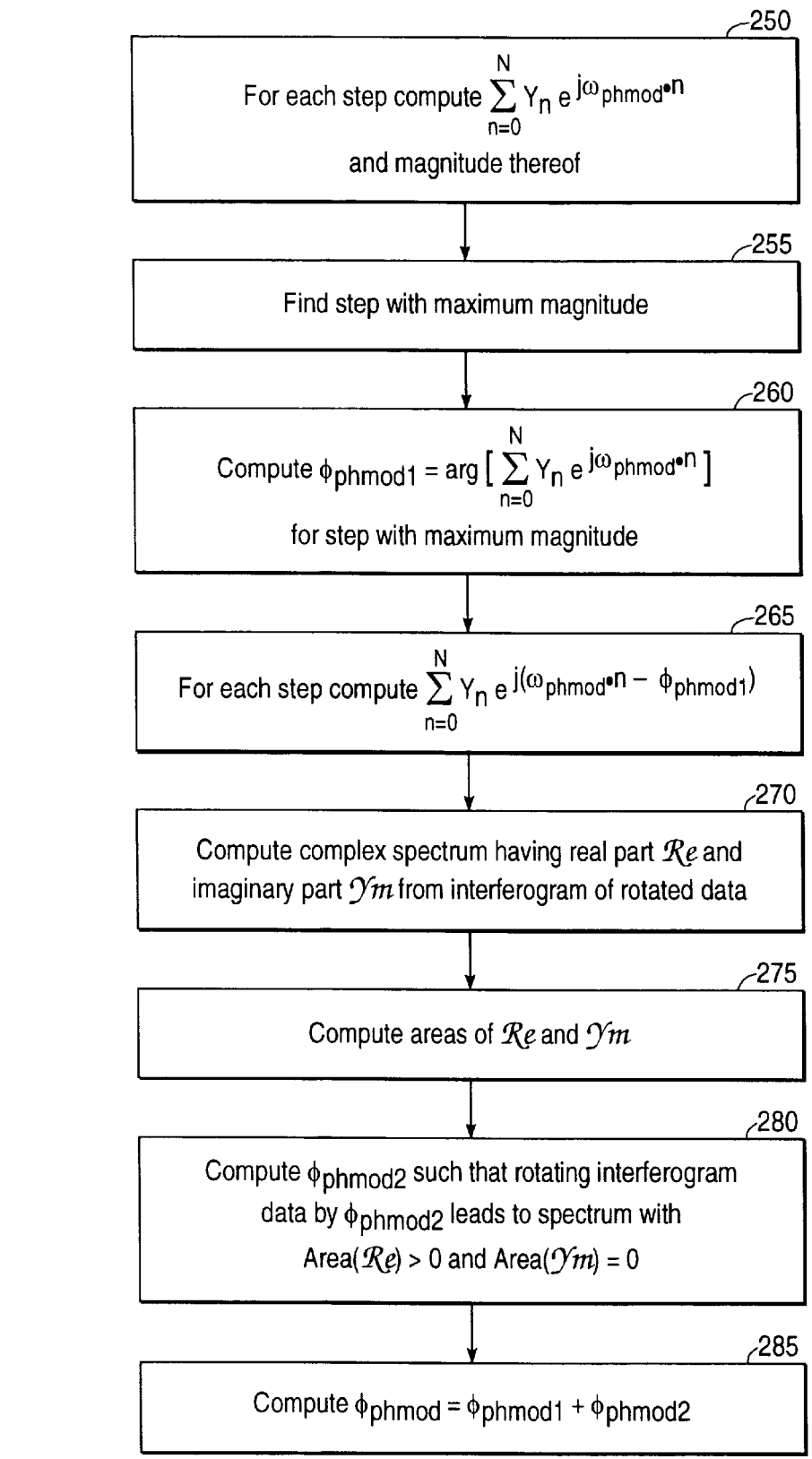
FIG. 16 is a flowchart view of a specific implementation for extracting the phase needed for demodulation at the phase modulation frequency.

FIG. 16 is a flowchart view of a specific implementation for complex multiplier 240 and processing block 245, which extract the phase $\phi_{phmod}$ for subsequent use in demodulation at the phase modulation frequency $\omega_{phmod}$. At a processing block 250, the $Y_n(\text{ref})$ data for all steps are demodulated using $\omega_{phmod}$ and the magnitudes of the sums are computed. Then, at a processing block 255, the step having the largest magnitude is determined, and at a processing block 260, an initial estimate $\phi_{phmod1}$ is determined by computing the argument of the DFT for the step having the largest magnitude. Then, at a processing block 265, this value is used to rotate the DFTs for each step.

Next, at a processing block 270, a complex interferogram is assembled from the rotated data, and the corresponding complex spectrum is computed. The spectrum of the real part of the interferogram is computed with Mertz phase correction and the phase array is stored to compute the spectrum of the imaginary part of the interferogram using the same peak location. The complex spectrum has real and imaginary parts. At a processing block 275, respective areas of the real and imaginary parts of the spectrum are computed over the spectral region of interest.

At a processing block 280, an angle $\phi_{phmod2}$ is determined such that when the previously rotated interferogram data is further rotated by this angle, and the spectrum recomputed, the area of the imaginary part of the spectrum is zero. Since the Fourier transform is a linear process, this can be accomplished simply by finding the argument of the complex number whose real part is the area of the real part of the spectrum and whose imaginary part is the area of the imaginary part of the spectrum (using the arctangent of the ratio). Once this angle $\phi_{phmod2}$ is found, the desired phase $\phi_{phmod2}$ is given by:

$$\phi_{phmod} = \phi_{phmod1} + \phi_{phmod2} \qquad (5)$$

If the reference sample had a known fixed phase shift as opposed to a phase shift of zero, Equation 5 would be modified to take the reference phase shift into account.

Figure 17:
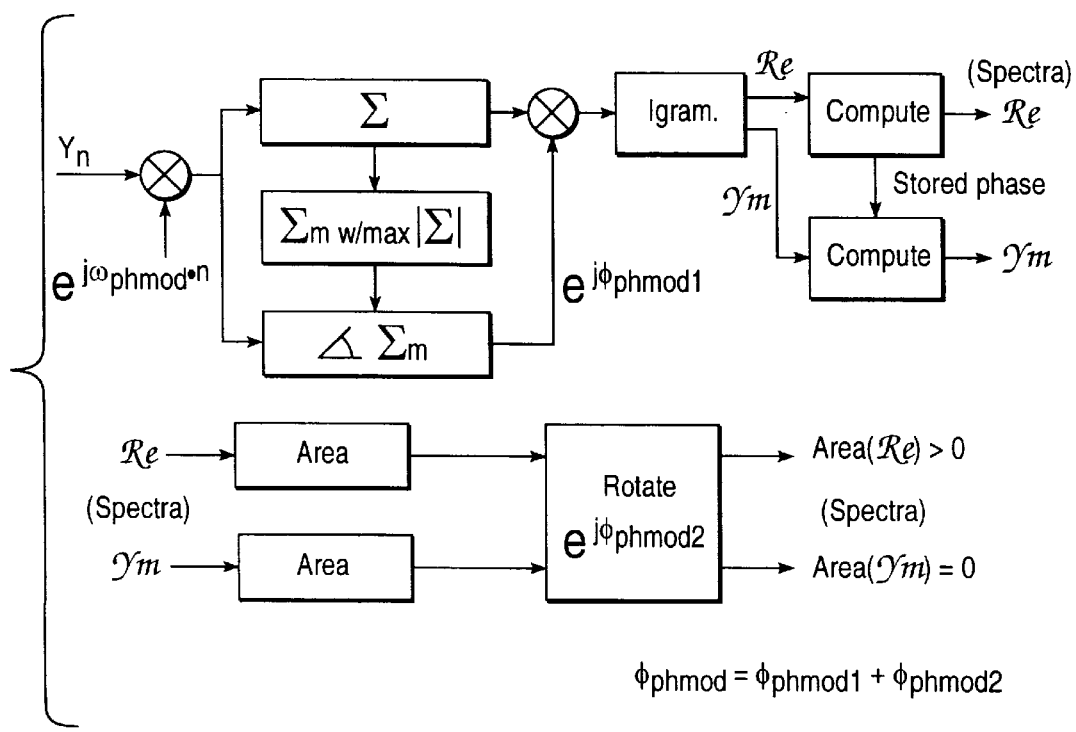
FIG. 17 is a block diagram view of the specific implementation of FIG. 16.

FIG. 17 is a block diagram view of processing block 245, showing the processing of the $y_n(\text{ref})$ data to extract the phase $\phi_{phmod}$ for subsequent demodulation of sample data at the phase modulation frequency $\omega_{phmod}$. The computations carried out by the various blocks in the figure can be determined from the description in connection with FIG. 16.

The determination of the phase $\phi_{sample}$ is carried out the same way, but an additional difficulty appears because $\omega_{sampling}$ is in general a low frequency, and the PM subcarrier is more than an order of magnitude larger amplitude, and thus its sidelobes generate a large baseline shift at the sample modulation frequency. This effect can be minimized by a baseline correction, which is described in the section below.

Baseline Correction

Figure 18:
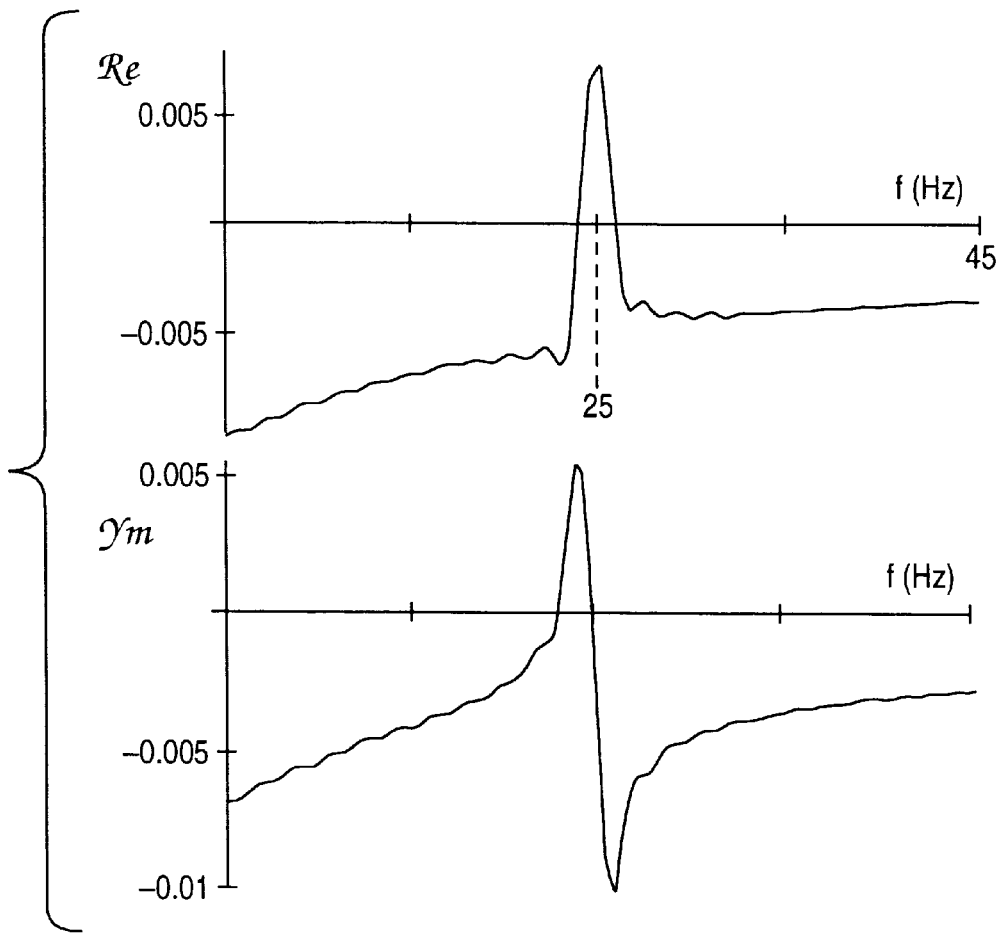
FIG. 18 shows the real and imaginary parts of the spectrum of a signal at the sample modulation frequency, illustrating the baseline shift problem.

FIG. 18 shows the real and imaginary parts of the spectrum of a signal at the sample modulation frequency without any attempt to correct the baseline problem. As mentioned above, the demodulation at the sample modulation frequency needs special care due to this baseline shift at the sample modulation frequency. The figure illustrates the possible severity of the problem. A typical desired measured value may be obtained by taking the peak value of the real part (relative to 0), which in this case would be approximately a factor of 2 lower than the "actual" value of the peak relative to the baseline. In the absence of knowledge of the fact of the baseline, certain measurements could be severely flawed without any warning that the data was suspect.

Figure 19:
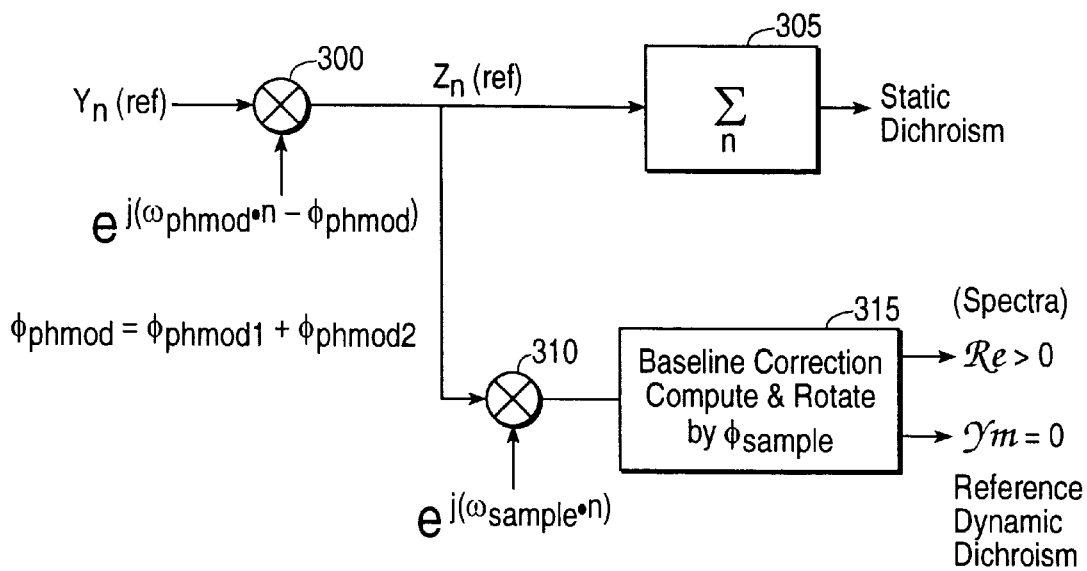
FIG. 19 is a block diagram showing a portion of the DSP for determining the baseline shift and extracting the phase needed for demodulation at the sample modulation frequency.

FIG. 19 is a block diagram showing a portion of the DSP for extracting the phase $\phi_{sample}$ needed for demodulation at the sample modulation frequency $\omega_{sample}$. The figure shows input samples $Y_n(\text{ref})$, which have been demodulated using the previously determined values for $\omega_{pem}$ and $\phi_{pem}$ (separately determined for each step). Samples $Y_n(\text{ref})$ are communicated to a phase modulation complex multiplier 300, which uses the known value for $\omega_{phmod}$ and the previously determined value for $\phi_{phmod}$. The output values from complex multiplier 300, designated $Z_n(\text{ref})$, are communicated to a summing block 305 and to a sample modulation complex multiplier 310. Complex multiplier 310 uses only the known value for $\omega_{sample}$ since $\phi_{sample}$ is not yet known. The output values from complex multiplier 310 are communicated to a processing block 315. Processing block 315 uses the $Z_n(\text{ref})$ data, demodulated at $\phi_{sample}$ to compute the baseline correction and compute the desired $\phi_{sample}$ value.

Figure 20:
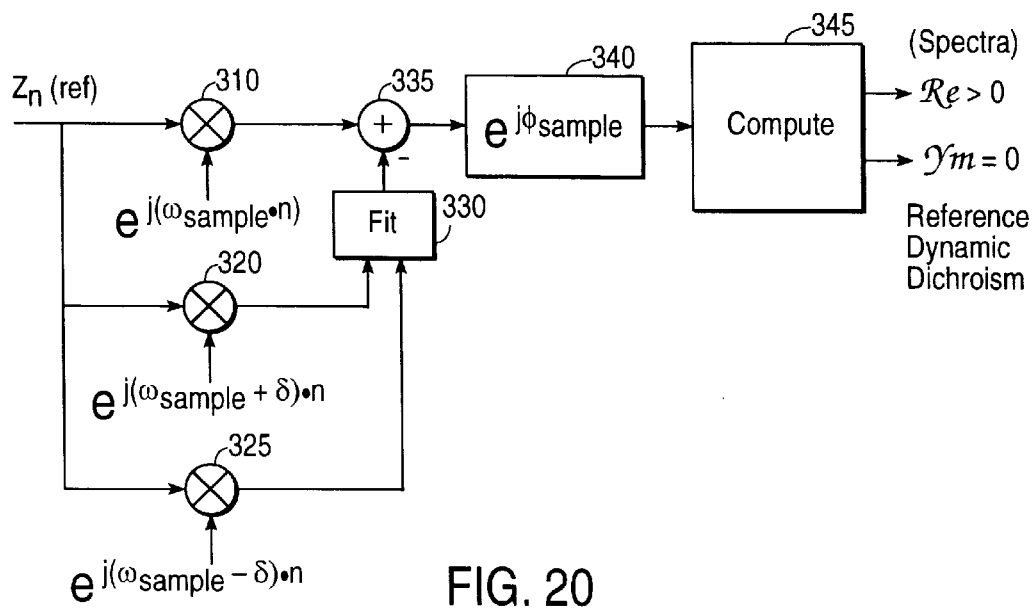
FIG. 20 is a block diagram showing additional details of the baseline correction DSP.

FIG. 20 is a block diagram showing additional details of the baseline correction DSP. Processing is along the lines shown in U.S. Pat. No. 5,612,784 [Curbelo97]. In short, the technique assumes that the baseline is a function that varies slowly with frequency, which is a sound assumption based on FIG. 18. The technique fits a complex function to the baseline in regions at lower and higher frequencies than the sample modulation frequency $\omega_{sample}$, since the argument varies with frequency. This function can be a straight line or a higher-order polynomial.

As shown in FIG. 20, the $Z_n(\text{ref})$ values are demodulated at frequencies above and below $\omega_{sample}$. In the particular implementation, in addition to being communicated to complex multiplier 310 (FIG. 19), the values are communicated to complex multipliers 320 and 325, which use frequencies ($\omega_{sample}+\delta$) and ($\omega_{sample}-\delta$), respectively. The resulting demodulated signals are communicated to a processing block 330, which determines the complex function that represents the baseline. The value of the complex baseline function at the sample modulation frequency is communicated to a complex adder, and is subtracted from the demodulated value of the signal output from complex multiplier 310.

If a straight line is used for the baseline correction, it can be defined by two points in the spectrum at either side of the frequency of interest. To reduce the noise contribution from the baseline correction, these values could each be the average of several spectral values or the values of spectral elements obtained at a lower spectral resolution.

The above baseline correction is applied to the data at each step for the reference sample, and the phase $\phi_{sample}$ for the sample modulation frequency demodulation is determined in the same manner as described in connection with determining $\phi_{phmod}$. This is shown schematically by a blocks 340 and 345 signifying determining a phase angle by which to rotate the data so that the area of the computed real spectrum is positive and the area of the computed imaginary spectrum is zero. These two blocks correspond to the mored detailed views of FIGS. 16 and 17, but using $\omega_{sample}$ to compute $\phi_{sample}$ instead of using $\omega_{phmod}$ to compute $\phi_{phmod}$.

With all phases known, the demodulation of the data from a sample can be implemented as in FIG. 13. When demodulating the sample modulation, the baseline correction has to be applied to obtain the correct value of the interferogram at each step.

Figure 21:
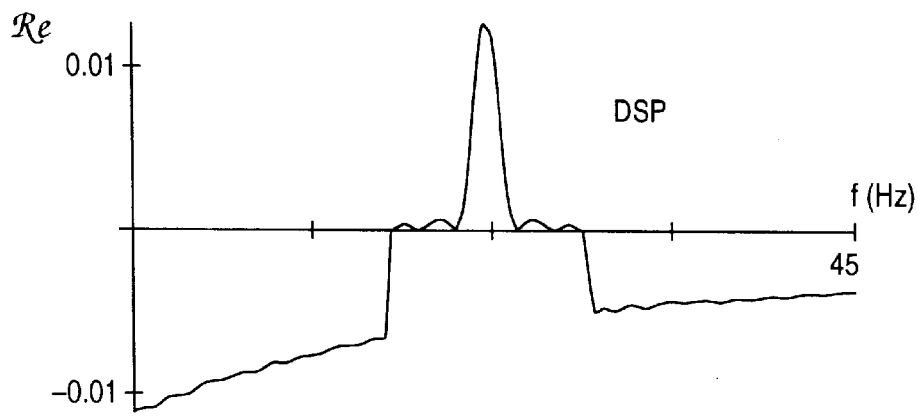
FIG. 21 shows the transform of the data from one step around the frequency of the sample modulation after baseline correction and rotation.

FIG. 21 shows the transform of the data from one step around the frequency of the sample modulation after baseline correction and rotation. As can be seen, the baseline has been removed so that the peak value relative to 0 represents the true value.

Figure 22:
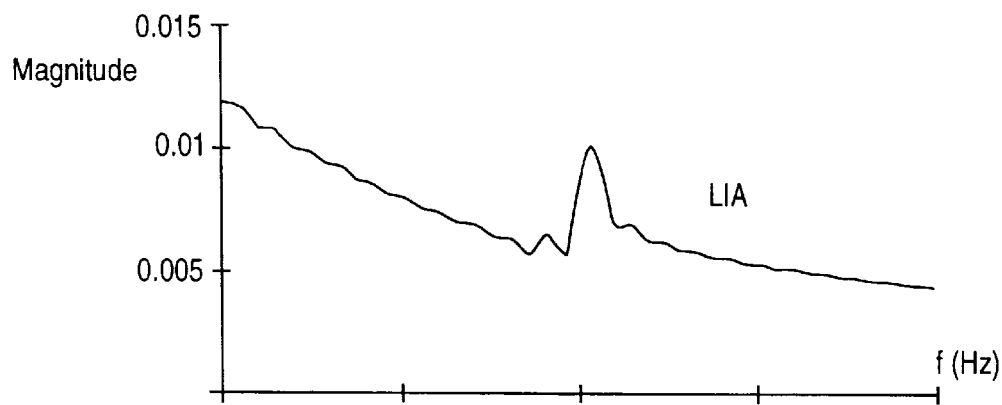
FIG. 22 shows a magnitude spectrum as would be measured using a lock-in amplifier (LIA).

FIG. 22 shows a magnitude spectrum as would be measured using a lock-in amplifier (LIA) measuring the amplitude at the sample modulation frequency. The LIA will report the total amplitude at that frequency. Since the amplitude (without baseline correction) includes the baseline offset, the LIA result will significantly overestimate the "true" value.

Specific Hardware and Software Configuration

The measurements were performed with a Bio-Rad FTS 6000 FT-IR spectrometer (Digilab Division of Bio-Rad Laboratories, Inc, 237 Putnam Avenue, Cambridge, Mass. 02139) using a Hinds PEM-80 ZS photoelastic modulator (Hinds Instruments, Inc., 3175 NW Aloclek Drive, Hillsboro, Oreg. 97124). The spectrometer was configured with a water-cooled ceramic mid-infrared source and a KBr substrate beamsplitter. Bio-Rad Win-IR Pro software, a Windows NT native application coded in Visual C++, was used to control the spectrometer. The data station was a DEC Celebris XL 5100 Pentium-based PC configured with 32 megabytes of RAM.

REFERENCES

[Curbelo92] U.S. Pat. No. 5,166,749, issued Nov. 4, 1992 to Raul Curbelo and David B. Johnson, for "Step Scanning Technique for Interferometer."

[Curbelo93a] U.S. Pat. No. 5,262,635, issued Nov. 16, 1993 to Raul Curbelo, for "Technique for Correcting Non-Linearity in a Photodetector Using Predefined Calibration Information."

[Curbelo93b] U.S. Pat. No. 5,265,039, issued Nov. 23, 1993 to Raul Curbelo and Warren R. Howell, for "Technique for Improving the Resolution of an A/D Converter."

[Curbelo96] U.S. patent application Ser. No. 08/712,940, filed Sep. 13, 1996 by Raul Curbelo, for "Triple Modulation Experiment for a Fourier Transform Spectrometer."

[Curbelo97] U.S. Pat. No. 5,612,784, issued Mar. 18, 1997 to Raul Curbelo, for "Digital Signal Processing for a FT-IR Spectrometer Using Multiple Modulations."

[Hinds88] Hinds International, Inc., PEM-80 *Photoelastic Modulator Systems Catalog*, 1988 (cover and introductory page plus pages numbered 1–21).

[Kam95] P. Y. Kam, *Performance of BPSK with open-loop tanlock carrier recovery*, Electronics Letters Online No. 19950227 (1995).

[Manning93] Christopher J. Manning and Peter R. Griffiths, *Step-Scanning Interferometer with Digital Signal Processing*, Applied Spectroscopy, Vol. 47, No. 9, Pages 1345–1349 (1993).

[Noda88] Isao Noda, A. E. Dowrey, and Curtis Marcott, *A Spectrometer for Measuring Time-Resolved Linear Dichroism Induced by a Small-Amplitude Oscillatory Strain*, Applied Spectroscopy, Vol. 42, No. 2, pages 203–216 (1988).

[Tervo93] Richard Tervo and Rogerio A. Enriquez, *Analysis of Digital Tanlock Loop with Adaptive Filtering*, IEEE Pacific Rim Conference on Communications, Computers and Signal Processing, Vol. 1, Pages 5–8 (1993).

Conclusion

While the above is a complete description of specific embodiments of the invention, various modifications, alternative constructions, and equivalents may be used.

For example, as mentioned above, it is possible to collect the sinusoidal reference signal from the PEM drive with a second digitizer channel in the spectrometer. Further, while specific DSP techniques for extracting the PEM frequency and phase were described above, the frequency and phase information can be extracted in the DSP process using one of the methods developed for communication systems ([Tervo93], [Kam95]). It is believed, however, that the embodiment described in detail above is superior because it can take into account all the data in the sampling interval since the computation is not being done in real time.

Additionally, while the invention was described in the context of a PEM drive signal that wasn't derived from the system clock and was not amenable to being locked to the system clock, the invention would have applicability to other signals where the frequency and phase of the carrier had to be derived from the detector signal itself. Further, while the PEM frequency extraction divided the sampling interval into four segments, there are other possibilities. However, there are practical constraints on M as discussed above. Moreover, there are potentially other ways to determine the phases $\phi_{phmod}$ and $\phi_{sample}$ used for the demodulations at $\omega_{phmod}$ and $\omega_{sample}$. At least for the former, the technique describe for extracting the PEM phase could be used. The difference is that the frequency is already known, being derived from the system clock, so there would be no need to successively refine estimates of the frequency.

Therefore, the above description should not be taken as limiting the scope of the invention as defined by the claims.

What is claimed is:

1. In a step-scanning Fourier transform spectrometer comprising an interferometer, a detector, and a digital processor, a digital method for extracting a modulation phase and modulation frequency of a modulation signal, the method comprising:

capturing a series of discrete digital values corresponding to an analog signal output from the detector, the series of discrete values having a time dependence over a sampling interval, which time dependence includes a component resulting from the modulation signal;

using a nominal modulation signal at a nominal modulation frequency to process at least some of the discrete values to determine a first phase error;

using the first phase error and the nominal modulation frequency to provide a first refined modulation frequency.

2. The method of claim 1, wherein the modulation signal is driving an element in the spectrometer optical train that modulates the polarization of a beam incident on the detector.

3. The method of claim 1, and further comprising adding a signal at the modulation frequency to the analog signal output from the detector before capturing the series of discrete digital values.

4. The method of claim 1, and further comprising:

using the the first refined modulation frequency to process at least some of the discrete values to determine a second phase error; and using the second phase error to modify the first refined estimate of the modulation frequency to provide a second refined estimate of the modulation frequency.

5. In a step-scanning Fourier transform spectrometer comprising an interferometer, a detector, and a digital processor, a digital method for generating spectral data from a sample, the method comprising:

passing a beam of analytic radiation through the interferometer and the sample to the detector;

using a modulation signal to subject the beam to a modulation at a modulation frequency prior to the beam encountering the detector;

for each of a plurality of retardation steps of the interferometer, capturing a series of discrete digital values corresponding to an analog signal output from the detector, the series of discrete values having a time dependence over a sampling interval, which time dependence includes a carrier component resulting from the modulation signal, extracting a modulation phase and modulation frequency of the carrier component from the series of discrete digital values, and using the modulation frequency and modulation phase extracted at that retardation step to demodulate the series of discrete digital values at that retardation step and provide at least one output value;

assembling the output values from the plurality of retardation steps to provide an interferogram; and computing a spectrum based on the interferogram.

6. The method of claim 5, wherein the modulation signal is driving an element in the spectrometer optical train that modulates the polarization of a beam incident on the detector.

7. The method of claim 5, and further comprising adding a signal at the modulation frequency to the analog signal output from the detector before capturing the series of discrete digital values.

8. In a step-scanning Fourier transform spectrometer comprising an interferometer, a detector, and a digital processor, a digital method for extracting a modulation phase and modulation frequency of a modulation signal, the method comprising:

capturing a series of discrete digital values output from the detector, the series of discrete values having a time dependence over a sampling interval, which time dependence includes a component resulting from the modulation signal;

using a nominal modulation signal at a nominal modulation frequency to process a first subset of the discrete values to determine a first phase error at a first particular point in the sampling interval;

using the first phase error and the nominal modulation signal to generate a phase-shifted signal that is nominally in phase with the modulation signal at the first particular point in the sampling interval;

using the phase-shifted signal to process a second subset of the discrete values to determine a second phase error at a second particular point in the sampling interval; and using the second phase error to modify the nominal modulation frequency to provide a first refined estimate of the modulation frequency.

9. The method of claim 8, and further comprising:

using a signal at the first refined estimate of the modulation frequency to process the first subset of the discrete values to determine a first refined phase error;

using the first refined phase error to generate a first refined phase-shifted signal; and using the first refined phase-shifted signal to process a subset of discrete values other than the first subset to determine a second refined phase error; and using the second refined phase error to modify the first refined modulation frequency to provide a second refined estimate of the modulation frequency.

10. In a step-scanning Fourier transform spectrometer comprising an interferometer, a detector, and a digital processor, a method for measuring a spectral response of a sample to multiple modulations, including a phase modulation, a polarization modulation, and a sample modulation, said method comprising:

passing a beam of analytic radiation through the interferometer and the sample to the detector;

using a phase modulation signal to subject the beam to a modulation at a known phase modulation frequency prior to the beam encountering the detector;

using a sample modulation signal to subject the sample to a modulation at a known sample modulation frequency prior to the beam encountering the detector;

using a polarization modulation signal to subject the beam to a modulation at a polarization modulation frequency prior to the beam encountering the detector;

for each of a plurality of retardation steps of the interferometer, capturing a series of discrete digital values corresponding to an analog signal output from the detector, the series of discrete values having a time dependence over a sampling interval, which time dependence includes a carrier component resulting from the polarization modulation signal, extracting a polarization modulation phase and polarization modulation frequency of the carrier component from the series of discrete digital values, and using the known phase modulation frequency, the known sample modulation frequency, and the polarization modulation frequency and polarization modulation phase extracted at that retardation step to demodulate the series of discrete digital values at that retardation step and provide a set of output values;

assembling the respective sets of output values from the plurality of retardation steps to provide a set of interferograms; and computing a set of spectra based on the interferograms.

11. The method of claim 10, wherein the modulation signal is driving an element in the spectrometer optical train that modulates the polarization of the beam incident on the detector.

12. The method of claim 10, and further comprising adding a signal at the polarization modulation frequency to the analog signal output from the detector before capturing the series of discrete digital values.

13. The method of claim 10, and further comprising correcting at least one of the sets of output values for a baseline component.

14. The method of claim 13, wherein the baseline component is determined by demodulating a set of discrete digital values at frequencies above and below the sample modulation frequency.

15. The method of claim 10, and further comprising calibrating the spectrometer by using a reference sample to determine a phase modulation rotation angle and a sample modulation rotation angle for use in demodulating the discrete digital values.

* * * * *